US008108032B2

(12) United States Patent
Onimura et al.

(10) Patent No.: US 8,108,032 B2
(45) Date of Patent: Jan. 31, 2012

(54) OPTICAL COHERENT TOMOGRAPHY DIAGNOSTIC APPARATUS

(75) Inventors: Yuuji Onimura, Tokyo (JP); Adrien E. Desjardins, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 532 days.

(21) Appl. No.: 12/274,991

(22) Filed: Nov. 20, 2008

(65) Prior Publication Data

US 2009/0143686 A1    Jun. 4, 2009

(30) Foreign Application Priority Data

Nov. 20, 2007    (JP) ................................. 2007-300930

(51) Int. Cl.
*A61B 6/00* (2006.01)
(52) U.S. Cl. ................. 600/476; 600/477; 600/478
(58) Field of Classification Search .......... 600/407–410, 600/473–480, 309–344; 606/1–19
See application file for complete search history.

(56) References Cited

U.S. PATENT DOCUMENTS

| | | | | |
|---|---|---|---|---|
| 6,002,480 A * | 12/1999 | Izatt et al. | ...................... | 356/479 |
| 6,134,003 A * | 10/2000 | Tearney et al. | ................ | 356/479 |
| 6,501,551 B1 * | 12/2002 | Tearney et al. | ................ | 356/477 |
| 6,615,072 B1 * | 9/2003 | Izatt et al. | ...................... | 600/478 |
| 6,687,010 B1 * | 2/2004 | Horii et al. | ..................... | 356/479 |
| 6,847,454 B2 * | 1/2005 | Crowley et al. | ............... | 356/479 |
| 7,006,231 B2 * | 2/2006 | Ostrovsky et al. | ............. | 356/479 |
| 2005/0274894 A1 | 12/2005 | Fujita | | |
| 2007/0159637 A1 * | 7/2007 | Toida | ............................. | 356/456 |
| 2007/0232890 A1 | 10/2007 | Hirota | | |

FOREIGN PATENT DOCUMENTS

| | | |
|---|---|---|
| EP | 1 962 082 A1 | 8/2008 |
| JP | 2001-527659 A | 12/2001 |
| WO | WO 2006/100544 A1 | 9/2006 |

OTHER PUBLICATIONS

Extended European Search Report dated Mar. 30, 2009 in corresponding European Application No. 08169539.7.

* cited by examiner

*Primary Examiner* — Sanjay Cattungal
(74) *Attorney, Agent, or Firm* — Buchanan Ingersoll & Rooney PC

(57) ABSTRACT

An optical coherent tomography diagnostic apparatus including: a light source; a splitter for splitting the light outputted from the light source into a measuring light and a reference light; a measuring light path; a reference light path; a probe inserted into a body cavity and emitting the measuring light to a subject of measurement; an image forming unit for calculating intensity distribution of the reflection light and for forming a tomographic image; a standard light path for transmitting standard light obtained by further splitting the light; wherein the light path length when exerting interference between the standard light and the reference light is approximately equal to the light path length when exerting interference between the reference light and the reflection light, and there is included a calculation unit for calculating time change of coherent light data obtained by exerting interference between the standard light and the reference light.

12 Claims, 15 Drawing Sheets

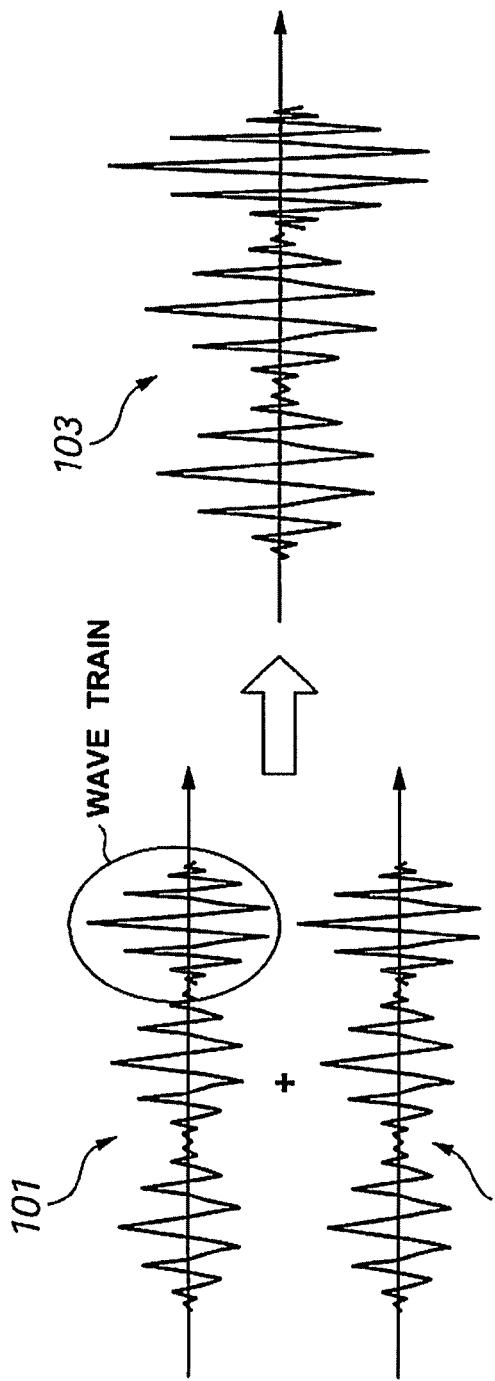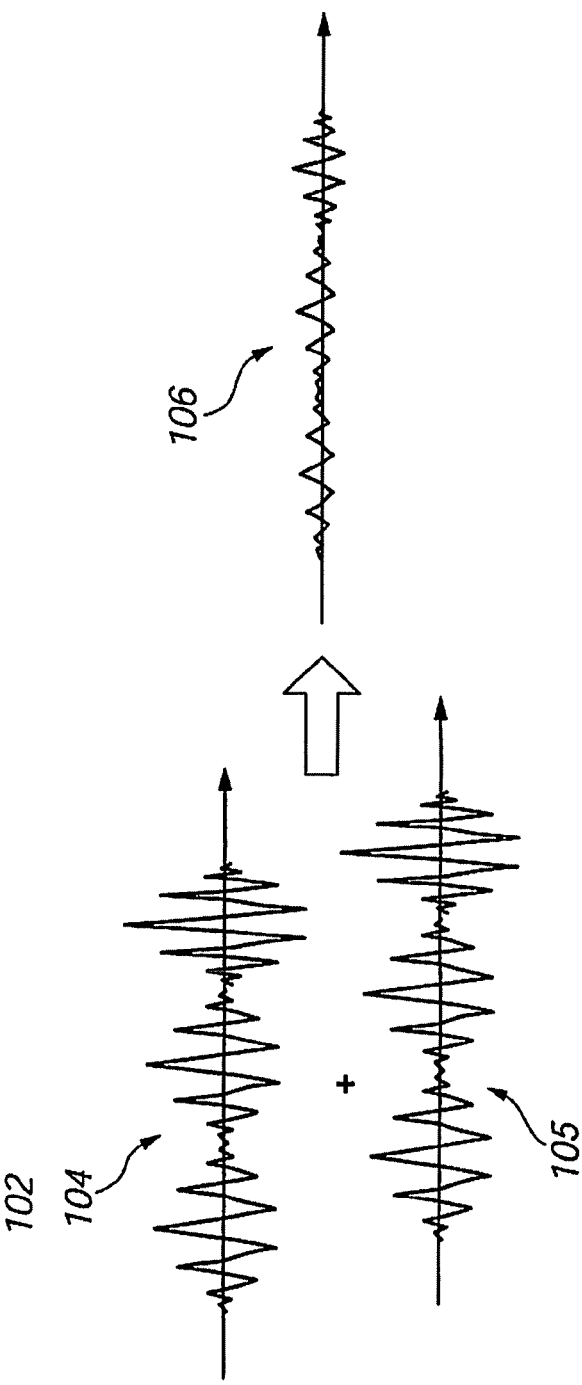

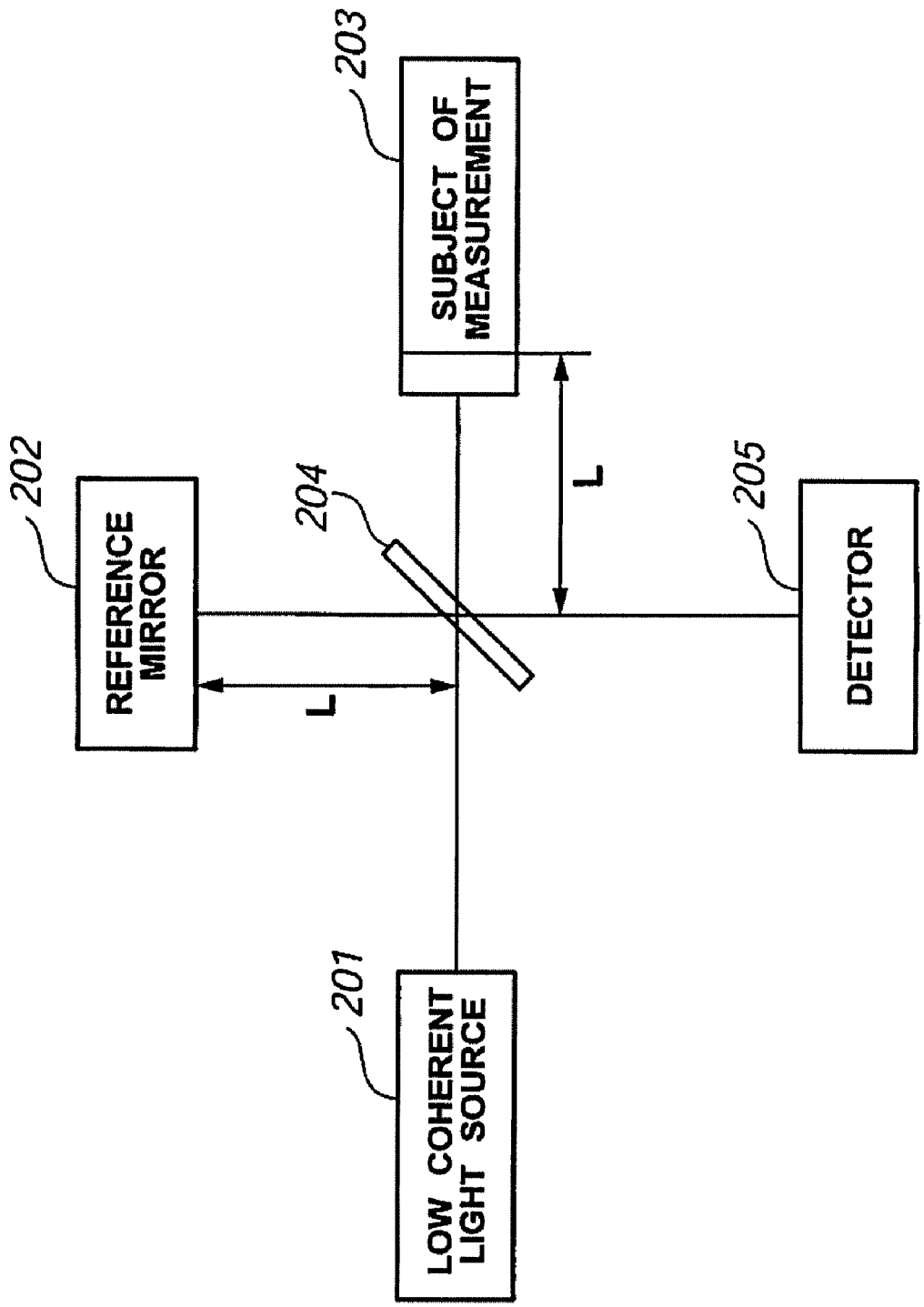

OPTICAL COHERENT TOMOGRAPHY DIAGNOSTIC APPARATUS

This application is based on Japanese Patent Application 2007-300930 filed Nov. 20, 2007, the entire contents of which are hereby incorporated by reference.

TECHNOLOGICAL FIELD

The subject matter disclosed here generally relates to a diagnostic apparatus. More specifically, the subject matter pertains to an optical coherent tomography diagnostic apparatus.

BACKGROUND DISCUSSION

In the past, there has been used an optical coherent tomography diagnosis apparatus (OCT: Optical Coherent Tomography) for arteriosclerosis diagnosis, for diagnosis before the surgery under an endovascular treatment by a high performance catheter such as a balloon catheter, a stent and the like, or for confirming the result thereof.

An optical coherent tomography diagnosis apparatus is an apparatus in which, in a state in which a catheter with a built-in optical lens and an optical fiber mounted with an optical mirror at the distal tip thereof is positioned in a blood vessel, measuring light is light-emitted in the blood vessel while rotating the optical mirror, radial scanning is carried out by receiving reflected light from biological tissue and a tomographic image of the blood vessel is created based on the coherent light by the interference between the reflection light obtained by the radial scanning and reference light split from the measuring light beforehand.

Further, there has been developed recently an optical coherent tomography diagnosis apparatus which utilizes wavelength-sweeping as an improved type of optical coherent tomography diagnosis apparatus.

The basic structure of the wavelength-sweeping optical coherent tomography diagnosis apparatus is similar to that of the optical coherent tomography diagnosis apparatus (OCT). The wavelength-sweeping optical coherent tomography diagnosis uses a light source having a longer wavelength than that of the optical coherent tomography diagnosis apparatus and also continuously light-emits lights having different wavelengths. Then, the mechanism for varying the light path length of the reference light is made unnecessary by obtaining reflection light intensity at each point in the depth direction of the biological tissue by using frequency analysis of the coherent light.

Here, with respect to any of the optical coherent tomography diagnostic apparatuses mentioned above, the amount of light of the measuring light (or the reflection light) or of the reference light and also the coherence performance thereof will largely affect the quality of the cross-section image visualized. Consequently, it is desirable for the light path to be such that the amount of measuring light (or reflection light) or reference light and also the coherence performance thereof will maintain a certain standard level.

On the other hand, depending on a use environment of the optical coherent tomography diagnostic apparatus or a transportation environment under the delivery thereof, it happens that the amplification performance and the coherence performance of the light source deteriorates as a result of the fact that a continuous vibration or the like is applied to the apparatus. Also, the amount of light of the measuring light (or the reflection light) or the reference light and also the coherence performance might be lowered as a result of the fact that affection is exerted on the state of the connection, the loss or the polarization of the optical fiber which forms the light path. In this case, the quality of the cross-sectional image visualized on the basis of the coherent light may be deteriorated.

Generally, there is a possibility that the quality deterioration of the cross-sectional image might lead to a fault diagnosis even if the deterioration is very little, so that in a case in which there exists deterioration, it becomes necessary for a user (doctor) to take treatments (various kinds of adjustments) for improving the amplification performance and the coherence performance of the light source and also for improving the state of the connection, the loss and the polarization of the optical fiber by calling a service person immediately (see Patent Document 1: Japanese PCT unexamined publication No. 2001-527659). If the deterioration of the cross-sectional image is relatively little, the user (doctor) may not realize such fact and so it can be assumed that the diagnosis will continue while the deteriorated cross-sectional image state is maintained.

SUMMARY

An optical coherent tomography diagnostic apparatus relating to the present invention includes such a constitution as described below. More specifically, the present invention relates to an optical coherent tomography diagnostic apparatus which including: a light source; a splitter for splitting the light outputted from the light source into a measuring light and a reference light; a measuring light path for transmitting the measuring light; a reference light path for transmitting the reference light; a probe inserted into a body cavity and emitting the measuring light to a subject of measurement; an image forming unit for calculating intensity distribution of the reflection light in the emission direction of the measuring light and for forming a tomographic image of the subject of measurement based on the intensity distribution by rendering the reflection light from the subject of measurement, which was obtained by the probe to have interference with the reference light; a standard light path for transmitting standard light obtained by further splitting the light outputted from the light source; wherein the light path length when exerting interference between the standard light and the reference light is approximately equal to the light path length when exerting interference between the reference light and the reflection light, and there is included a calculation unit for calculating time change of coherent light data obtained by exerting interference between the standard light and the reference light.

With the apparatus and method disclosed here, the user (doctor) can recognize objectively whether or not the amplification performance and the coherence performance of the light source and also the connection, the loss and the polarization state of the optical fiber are in normal (good) states. The user is able to recognize whether or not the state of the light path is normal.

BRIEF DESCRIPTION OF THE DRAWINGS

FIGS. 1a and 1b are diagrams explaining a measurement principle of an optical coherent tomography diagnosis apparatus.

FIG. 2 is a schematic illustration of basic principles of an optical coherent tomography diagnosis apparatus.

DETAILED DESCRIPTION

Figure 3:
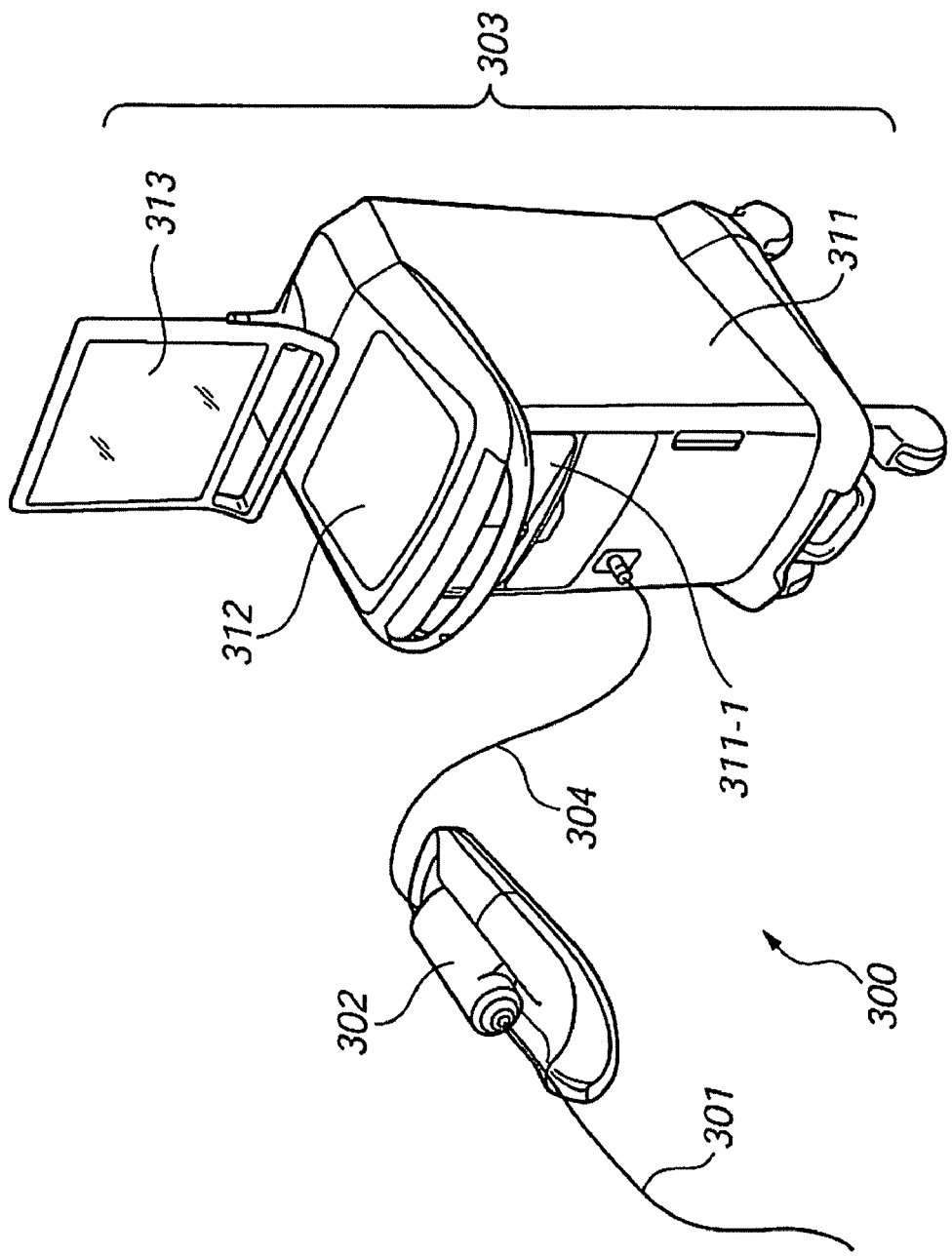
FIG. 3 is a perspective view of an optical coherent tomography diagnosis apparatus.

Hereinafter, respective exemplified embodiments of the diagnostic apparatus disclosed here will be described in detail with reference to the attached drawings.

1. Measurement Principle of Optical Coherent Tomography Diagnosis Apparatus

The general measurement principle of an optical coherent tomography diagnosis apparatus is as follows. Generally, light is an electromagnetic wave and so it has a characteristic of exerting interference in the case of being mixed. The interference performance of easy-to-interfere or hard-to-interfere is also referred to as coherence and in a general optical coherent tomography diagnosis apparatus, coherent light having low coherence (low coherent light) is utilized.

The low coherent light becomes a random signal as shown by 101, 102 in FIG. 1a which illustrates a graph with time along the horizontal axis and electric field along the vertical axis. Respective peaks in the same drawing are referred to as a wave train and the respective wave trains possess mutually independent phases and amplitudes. For this reason, as shown in FIG. 1a, in a case in which the same wave trains overlap, constructive interference (between 101 and 102) occurs and the two waves are additive in effect as represented at 103. On the other hand, in a case in which there is a very little time delay (between 104 and 105 in FIG. 1b), cancellation of the two waves tends to occur and a constructive interference will not be observed (see 106 in FIG. 1b). Rather a sort of destructive interference occurs in which the two waves tend to counteract one another as represented at 106 in FIG. 1b.

The optical coherent tomography diagnosis apparatus is an apparatus utilizing this characteristic and FIG. 2 shows a basic principle of the apparatus. Light outputted from a low coherent light source 201 is split by a beam splitter 204 and respective beams are directed to a reference mirror 202 and the subject of measurement 203. At that time, reflected light returned from the subject of measurement side includes reflected light from various positions such as light reflected by a material body surface, light reflected by a shallow position inside the material body, light reflected by a deep portion inside the material body and the like.

However, the incident light is low coherent light, so that when distance from the beam splitter 204 to the reference mirror 202 is L and the coherent length is ΔL, the reflection light whose interference can be observed only becomes a reflection light from a reflection surface which exists at a position whose distance from the beam splitter 204 is L+ΔL/2.

Consequently, if the distance from the beam splitter 204 to the reference mirror 202 is changed, it is possible for a detector 205 to selectively detect only the reflection light from the reflection surface inside the material body corresponding to the distance thereof. Then, it is possible, based on the intensity of the reflection light in response to each distance, to form a tomographic image by making information about the structure inside the material body visible.

2. Appearance Configuration of Optical Coherent Tomography Diagnosis Apparatus

FIG. 3 schematically illustrates features of an optical coherent tomography diagnosis apparatus (300) according to a first embodiment disclosed by way of example here.

As shown in FIG. 3, the optical coherent tomography diagnosis apparatus (300) includes a catheter unit 301, a scanner/pullback unit 302 and an operation control unit 303. The scanner/pullback unit 302 and the operation control unit 303 are connected by a signal wire 304.

The catheter unit 301 is inserted into a blood vessel directly and measures a state inside the blood vessel by using an optical probe. The scanner/pullback unit 302 is detachable with respect to the catheter unit 301, has a built-in motor and defines the radial operation of the optical probe in the catheter unit 301.

When executing an optical coherence tomography diagnosis in the blood vessel, the operation control unit 303 includes a function for inputting various kinds of setting values and a function for processing data obtained by the measurement and for displaying them as a tomographic image.

In the operation control unit 303, 311 denotes a main body control unit, which processes the data obtained by the measurement, outputs the processed result and the like, and 311-1 denotes a printer/DVD-recorder, which prints the processed result in the main body control unit 311, stores it as data and the like.

The operation control unit 303, 311 also includes an operation panel 312 at which the user inputs various kinds of setting values, and a LCD monitor 313 serving as a display device, which displays the process result in the main body control unit 311.

3. Features of Optical Coherent Tomography Diagnosis Apparatus

Figure 4:
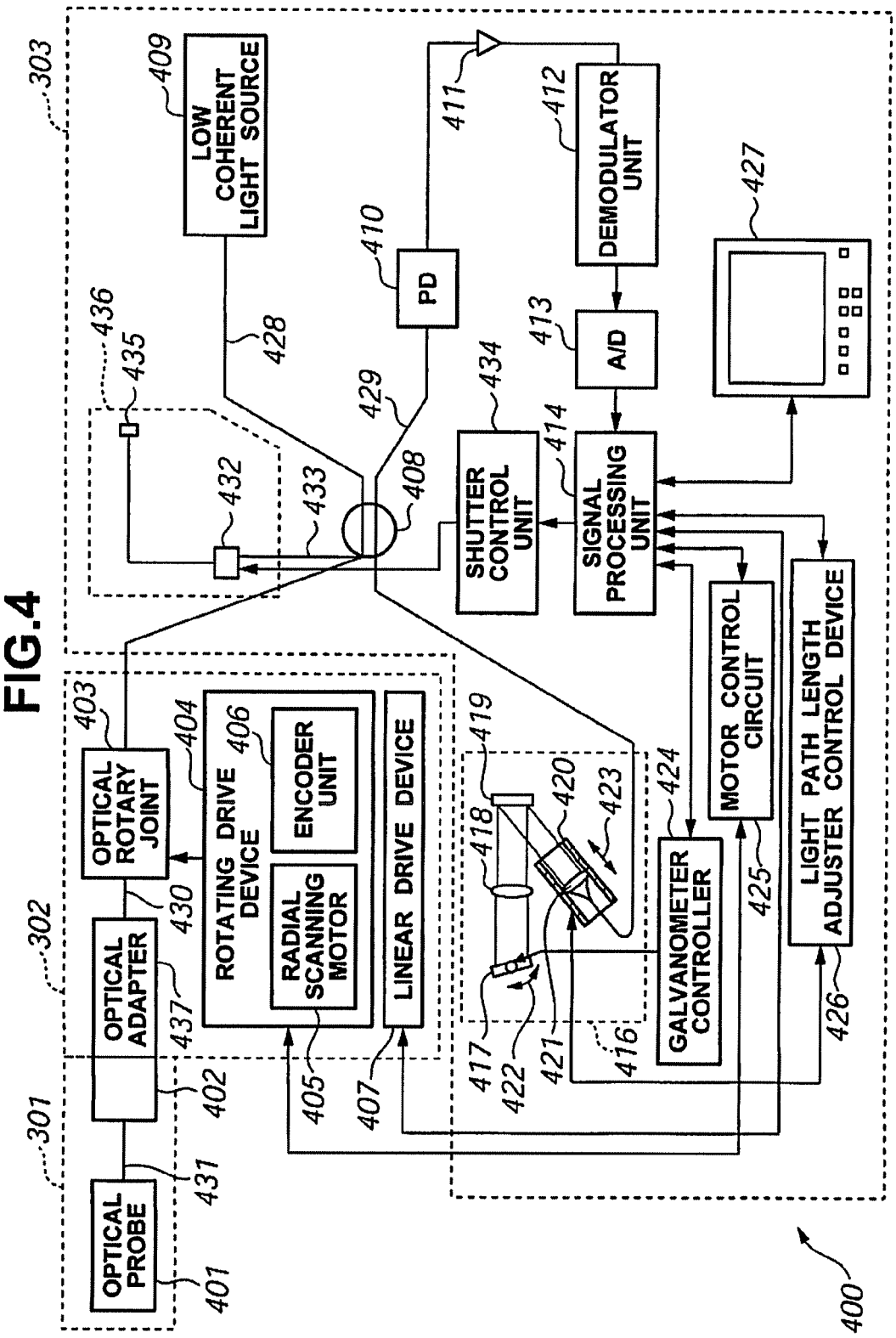
FIG. 4 is a schematic illustration of features of an optical coherent tomography diagnosis apparatus according to a first exemplified embodiment disclosed here.

Features and operational aspects of the optical coherent tomography diagnosis apparatus (300) will be described below in connection with an example of one embodiment illustrated in FIG. 4.

The apparatus 400 includes a low coherent light source 409 such as a super high luminosity light-emitting diode or the like. The low coherent light source 409 outputs a low coherent light which shows coherence only in a short distance range such that the wavelength thereof is around 1310 nm and the coherent distance (coherent length) thereof is around a few μms to a few tens of μms.

For this reason, when this light is split into two paths and thereafter mixed again and when the difference of the two light path lengths from the splitting point to the mixing point is within a short distance range such as around a few μms to a few tens of μms (i.e., when the light path length when exerting interference between the standard light and the reference light is approximately equal to a light path length when exerting interference between the reference light and the reflection light), a coherent light is detected. When the difference of the light path lengths is larger than that, coherent light cannot be detected.

The light of the low coherent light source 409 enters one end of a first single-mode fiber 428 and is transmitted to the distal surface side thereof. The first single-mode fiber 428 is optically coupled with a second single-mode fiber 429 and a third single-mode fiber 433 at an optical coupler unit 408 on the way.

The optical coupler unit is an optical component which, for example, can split one light signal into two or more outputs, and can combine two or more inputted light signals into one output. The light of the low coherent light source 409 is split into three light paths at the maximum by the optical coupler unit 408 and can be transmitted thereby.

It should be noted that a coupling point of a third single-mode fiber 433 is not limited by an optical coupler portion 408 and it is possible for the coupling point to be on a first single-mode fiber 428, on the light path length from the optical coupler portion 408 to a variable mechanism 416 or on the light path from the optical coupler portion 408 to the scanner/pullback unit 302.

On the distal side (in the measuring light path) from the optical coupler unit 408 of the first single-mode fiber 428, there is provided with the scanner/pullback unit 302. In the inside of the scanner/pullback unit 302, there is provided with an optical rotary joint 403 for attaining coupling between a non-rotation unit and a rotation unit and for transmitting the light.

Further, at the distal side of a fourth single-mode fiber 430 in the optical rotary joint 403, a connector portion 402 of the catheter unit 301 is detachably connected with respect to an optical adapter unit 437 of the scanner/pullback unit 302. Thus, the light is transmitted from the low coherent light source 409 to a fifth single-mode fiber 431 which is inserted into an optical probe 401 repeating light transmission and reception and which is rotatingly drivable.

The light transmitted to the fifth single-mode fiber 431 illuminates the biological tissue in a blood vessel from the distal side of the optical probe 401 while being scanned radially. Then, a portion of the reflected light diffused on the surface or in the inside of the biological tissue is taken-in by the optical probe 401 and returns to the first single-mode fiber 428 side along a reverse light path. A portion of the returned light is shifted to the second single-mode fiber 429 side by the optical coupler unit 408, is emitted from one end of the second single-mode fiber 429 and is received by a photodetector (for example, photodiode 410).

The rotation unit side of the optical rotary joint 403 is rotatingly driven by a radial scanning motor 405 of a rotating drive device 404. Also, the rotation angle of the radial scanning motor 405 is detected by an encoder unit 406. Further, the scanner/pullback unit 302 includes a linear drive device 407 which effects the operation (movement in the axial direction) in the insertion direction (deletion direction and its opposite direction in the coelom) of the catheter unit 301 based on the instruction from the signal processing unit 414. The movement in the axial direction is realized by a fact that the linear drive device 407 operates so as to move the scanner including the optical rotary joint 403 based on a control signal from the signal processing unit 414.

On the other hand, on the distal side (in reference to the light path direction) of the optical coupler unit 408 of the second single-mode fiber 429, a variable mechanism 416 of the light path length is provided for changing the light path length of the reference light.

This light path length variable mechanism 416 includes a first light-path length changer for changing the light path length corresponding to an inspection range in the depth direction (emission direction of measuring light) of the biological tissue high-speedily, and a second light-path length changer for changing the light path length corresponding to fluctuation of the lengths thereof so as to absorb the fluctuation of the lengths of individual optical probes in case of exchanging optical probes.

Facing the distal tip of the second single-mode fiber 429 is a grating 419. The grating 419 is mounted on one axis stage 420 together with the distal tip of the second single-mode fiber 429 and is arranged through a collimating lens 421 freely movable in a direction shown by an arrow 423. Also, a rotatable galvanometer 417 which is rotatable over a relatively small angle is mounted as a first light-path length changer through this grating 419 (diffractive grating) and a corresponding lens 418. This galvanometer 417 is rotated in a relatively high-speed manner in the direction indicated by the arrow 422 by a galvanometer controller 424.

The galvanometer 417 is a device that reflects light by means of a galvanometer mirror and it is constituted, by applying an alternate-current drive signal to the galvanometer which functions as a reference mirror, such that the mirror mounted on the movable portion thereof is rotated in a relatively high-speed manner.

In other words, a drive signal is applied from the galvanometer controller 424 to the galvanometer 417 so that the galvanometer 417 is rotated in a relatively high-speed manner in the arrow 422 direction by the drive signal so that the light path length of the reference light is changed in a high-speed manner as much as the light path length corresponding to the inspection range in the depth direction of the biological tissue. One cycle of the change of this light path difference becomes a cycle for obtaining coherent light for one line.

On the other hand, in situations in which the optical probe 401 is exchanged, the one axis stage 420 functions as a second light-path length changer having a variable range of the light path length such that fluctuations of the light path length of the optical probe can be absorbed. Further, the one axis stage 420 also functions as an adjuster for adjusting offset. For example, even in a case in which the distal tip of the optical probe 401 is not closely attached on (i.e., is not positioned close to) the surface of the biological tissue, it is possible, by changing the light path length in a quite small increment through the one axis stage 420, to set a state of exerting interference to the reflected light from the surface position of the biological tissue.

The light whose light path length is changed by the variable mechanism 416 of the light path length is mixed with the light obtained from the first single-mode fiber 428 side in the optical coupler unit 408 provided on the way of the second single-mode fiber 429 and is light-received by the photodiode 410 as a coherent light.

On the other hand, on the distal side of the third single-mode fiber 433 (in the standard light path), there is provided a standard light transmission mechanism 436 for transmitting the standard light which is used to confirm the amplification performance, the deterioration of the coherence performance of the light source and also the connection, the loss or the polarization state of the optical fiber (second single-mode fiber 429) forming the light path of the reference light.

The standard light transmission mechanism 436 is constituted such that the standard light split at the optical coupler portion 408 is reflected on a reflection mirror 435 and thereafter, the light path length until exerting interference with the reference light becomes equal to the light path length of the reference light in the optical coupler portion 408.

In the light path of the standard light, there is disposed a shutter portion 432. A shutter control unit 434 executes an open/close control operation of the shutter portion 432 based on an open/close instruction from the signal processing unit 414. The shutter portion 432 is in a closing (closed) state in a case in which the catheter unit 301 is connected to the scanner/pullback unit 302 and forms a cross-sectional image of the biological tissue (in the case of measurement mode). In the closed state, light is unable to pass the shutter 432. On the other hand, the shutter portion 432 is in an open state in a case in which the catheter unit 301 is disconnected and the connection, the loss or the polarization state of the optical fiber (second single-mode fiber 429) forming the amplification performance and the coherence performance of the light source, and the light path of the reference light is confirmed (in case of the check mode). Thus, in the check mode with the catheter unit 301 disconnected and the shutter portion 432 in the opened state, it is possible to predict or determine a number of different situations including the amplification performance and coherence performance which both indicate the state of the light source, and the connection state, loss state and polarization state of the second single-mode fiber 429.

The standard light reflected on the reflection mirror 435 in the inside of the standard light transmission mechanism 436 is mixed with the light obtained from the second single-mode fiber 429 side at the optical coupler portion 408 and is light-received by the photodiode 410 as a coherent light.

It should be noted that the standard light transmission mechanism 436, when transmitting the standard light, does not have a connection portion on the light path and does not have such a movable portion which changes the light path length either (i.e., the standard light path length is fixed). Consequently, there is little deterioration of the standard light caused by bad connection and the intensity or the coherence performance of the standard light is not significantly lowered.

In this manner, the coherent light received by the photodiode 410 (coherent light of measuring light and reference light in case of the measurement mode, and coherent light of reference light and standard light in case of the check mode) is converted photoelectrically and is amplified by an amplifier 411.

Thereafter, it is inputted to a demodulator unit 412 and in this demodulator unit 412, there is performed a demodulation process for extracting only a signal component of the coherent light. The output of the demodulator unit 412 is inputted to an A/D converter 413.

In the A/D converter 413, digital data of one line (coherent light data) is generated by sampling the coherent light signal for 200 points. The sampling frequency has a value obtained by splitting the time period of one scanning of the light path length by 200.

The coherent light data of one line unit which is generated in the A/D converter 413 is inputted to the signal processing unit 414. In the case of the measurement mode, in the signal processing unit 414, tomographic images at respective positions in the blood vessel are formed by converting the coherent light data in the depth direction of the biological tissue to video signals which are outputted by a predetermined frame rate to an LCD monitor 427.

In the case of a check mode, when the coherent light data is inputted to the signal processing unit 414, the time change of the coherent light data is calculated and the calculated result is graph-displayed on the LCD monitor 427. Also, the deterioration of the quality of the cross-sectional image extracted from the calculated result based on the coherent light is judged. The main cause of the deterioration of the quality of the light source lies in the deterioration of the amplification performance or the coherence performance. There is also a case in which the cause lies in the aggravation of the first single-mode fiber 428, the connection, the loss or the polarization state of the optical fiber forming the light path of the reference light. As an example, if there is a connection loss or an optical fiber loss, the strength of the light will decrease along the path. Thus, when measuring light is to be mixed with the reference light and exerts interference, the interference intensity is deteriorated.

Thus, it is possible for the user to recognize objectively whether or not the amplification performance and the coherence performance of the light source, and the connection, the loss or the connection state of the optical fiber are good.

The signal processing unit 414 is further connected with a light path length adjuster control device 426. The signal processing unit 414 carries out position control of the one axis stage 420 through the light path length adjuster control device 426. Also, the signal processing unit 414 is connected with a motor control circuit 425 and controls the rotational drive of the radial scanning motor 405.

Additionally, the signal processing unit 414 is connected with the galvanometer controller 424 which controls the scanning of the light path length of the reference mirror (galvanometer mirror). The galvanometer controller 424 outputs a drive signal to the signal processing unit 414 and the motor control circuit 425 is synchronized with the galvanometer controller 424 based on this drive signal.

4. Light Transmission Path in Optical Coherent Tomography Diagnostic Apparatus

The following is an outline of the transmission paths until the light is received by the photodiode 410 after the light outputted from the low coherent light source 409 is split and transmitted on the respective light paths in the optical coherent tomography diagnostic apparatus 300.

Figure 5:
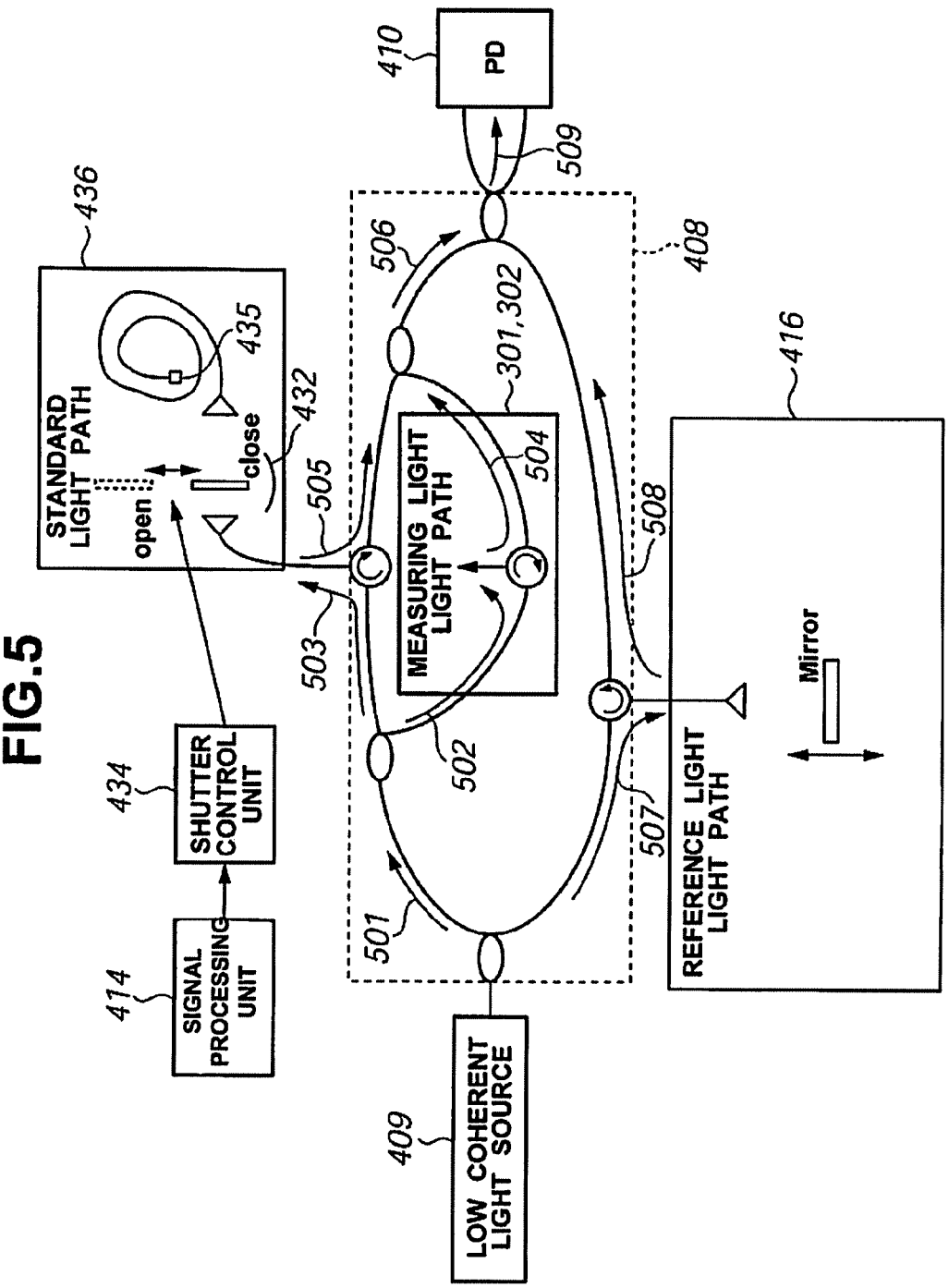
FIG. 5 is a schematic illustration of a transmission path in the optical coherent tomography diagnostic apparatus.

FIG. 5 schematically shows transmission paths of the measuring light, the reference light and the standard light in the optical coherent tomography diagnostic apparatus 300 relating to the present exemplified embodiment. As shown in FIG. 5, the light outputted from the low coherent light source 409 is inputted to the optical coupler portion 408.

Then, in case of a measurement mode, the measuring light is transmitted as 501→502→504→506, is mixed with the reference light transmitted as 507→508 and exerts interference therewith. The coherent light is transmitted in an arrow 509 direction and is light-received in the photodiode 410.

On the other hand, in case of a check mode, the standard light is transmitted as 501→503→505→506, is mixed with the reference light transmitted as 507→508 and exerts interference therewith. The coherent light is transmitted in the arrow 509 direction and is light-received in the photodiode 410.

5. Features of Signal Processing Unit 414

Figure 6:
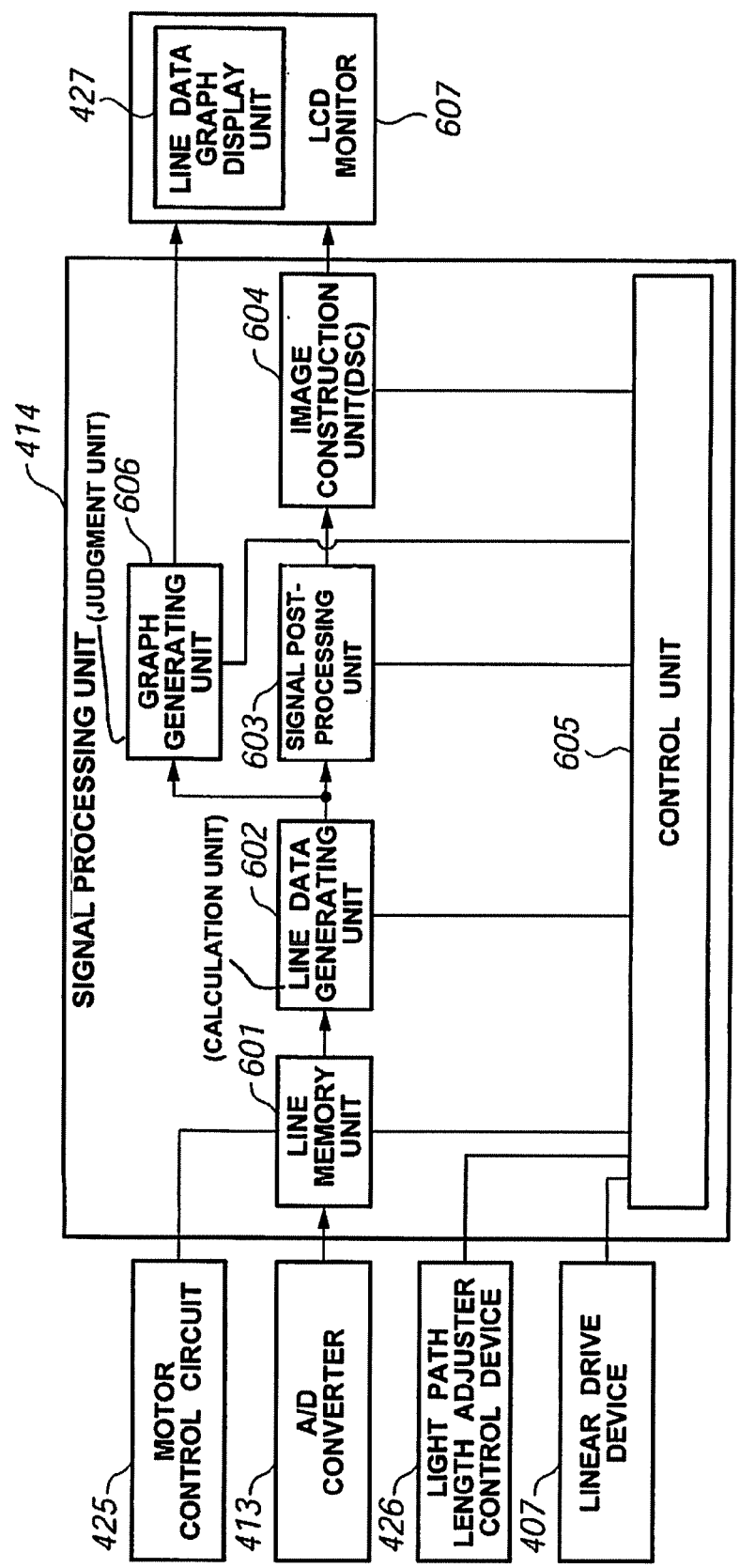
FIG. 6 is a schematic illustration of aspects of the signal processing unit generally illustrated in FIG. 5 and related function block.
Figure 7:
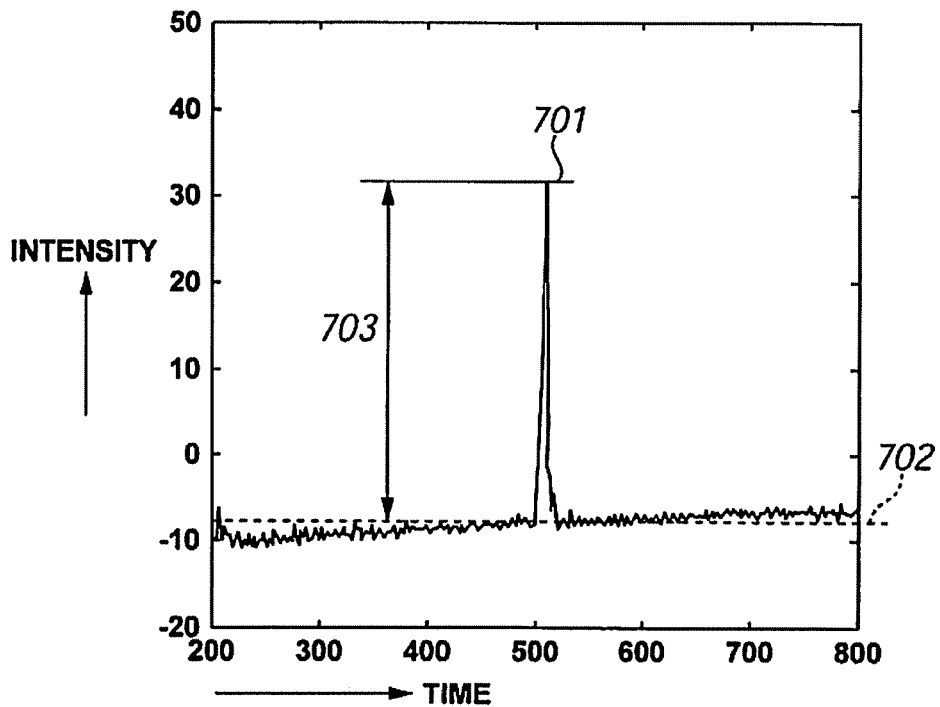
FIG. 7 is an example of a graph produced based on coherent light data inputted to the graph generating unit shown in FIG. 6.

Referring to FIG. 6, the following is an outline of a process performed in the signal processing unit 414 of the optical coherent tomography diagnostic apparatus 300. As illustrated, the signal processing unit 414 includes a control unit 605 connected to a line memory unit 601, a line data generating unit 602, a signal-post processing unit 603 and an image construction unit 604. In the case of the measurement mode, the coherent light data generated in the A/D converter 413 is processed in the line memory unit 601 such that the number of lines per one rotation of the radial scanning motor becomes 515 lines by using the signal of the encoder unit 406 of the radial scanning motor 405 outputted from the motor control circuit 425. Thereafter, the data is outputted to a line data generating unit of a succeeding stage. The line data generating unit 602 is an example of a calculation unit which calculates the time change of coherent light data obtained by exerting interference between the standard light and the reference light.

In the line data generating unit 602, a line addition-averaging processing, a filtering processing and a logarithmic conversion processing are implemented with respect to the coherent light data, line data is generated by generating coherent light intensity data in the depth direction of the biological tissue and thereafter the generated line data is outputted to a signal post-processing unit 603 of a succeeding stage. In the signal post-processing unit 603, a contrast adjustment, a luminance adjustment, a gamma correction, a frame correlation processing, a sharpness processing and the like are applied with respect to the line data which is then outputted to an image construction unit (DSC) 604.

In the image construction unit 604, it is converted to a video signal from the line data sequence of the polar coordinate and a cross-sectional image is displayed on the LCD monitor 427. It should be noted here that an embodiment in which an image is constituted from 512 lines is shown as one example, but it is not limited by only this number of lines.

On the other hand, in the check mode, the coherent light data generated in the A/D converter 413 is inputted to a graph generating or producing unit 606 via the aforementioned line memory unit 601 and the line data generating unit 602. The graph generating unit 606 is an example of a judgment unit for judging the state of the light path for transmitting the reference light based on the coherent light intensity.

In the graph producing unit 606, the time change of the coherent light data is calculated based on the inputted coherent light data, the maximum value is detected based on this and the coherent light intensity is calculated.

Also, it is judged whether or not the degree of deterioration of the coherent light intensity with respect to the standard intensity reaches a predetermined threshold or more by comparing the calculated coherent light intensity with a predetermined standard intensity. It should be noted that the detail of the processing in the graph producing unit 606 will be explained later.

The coherent light data graph display unit 607 is controlled so as to graph-display the time change of the coherent light data on the LCD monitor 427 and at same time, there are displayed the coherent light intensity and the degree of deterioration calculated in the graph producing unit 606, the standard intensity used for the calculation, the predetermined threshold and the like.

6. Details of Processing in Graph Producing Unit 606

Referring to FIG. 17, the following is an explanation of aspects of the processing in the graph producing unit 606. In the graph producing unit 606, first, the time change of the inputted coherent light data is calculated and the maximum value 701 is extracted based on this.

Further, within the coherent light data, an average value (702) of data portions excluding a maximum value 701 and the near data portions thereof is calculated. Then, the coherent light intensity 703 is calculated from the difference between the maximum value 701 and the average value 702.

Further, in the graph generating or producing unit 606, the coherent light intensity is compared with a predetermined standard intensity (intensity to be possessed by coherent light obtained by making interference between reference light and standard light). Then, there is obtained the degree to which the coherent light intensity 703 deteriorates with respect to the standard intensity (degree of deterioration) by calculating "100−(coherent light intensity/standard-intensity×100)".

Further, it is judged whether or not the obtained degree of deterioration is equal to or higher than a predetermined threshold and in a case in which it is equal to or higher than the predetermined threshold, it is judged that the amplification performance and the coherence performance of the light source, and also the connection, the loss or the polarization state of the optical fiber on the light path of the reference light are not normal. A message indicating that fact is outputted.

Figure 8:
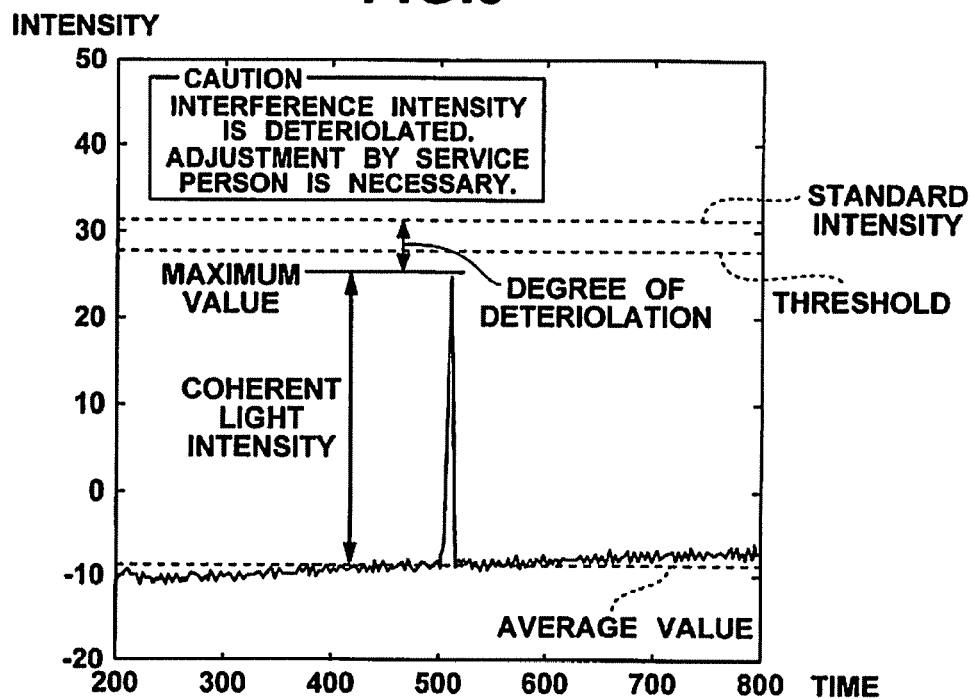
FIG. 8 is an example of graph-displayed coherent light data processed in the graph generating unit illustrated in FIG. 6.

FIG. 8 is a diagram showing an example of graph-displayed coherent light data processed in the graph generating unit 606. As shown in FIG. 8, there are displayed the extracted maximum value and the calculated average value. At the same time, there is displayed coherent light intensity. Also, the standard intensity is shown and the calculated degree of deterioration is displayed between the standard intensity and the maximum value. Further, in a case in which the degree of deterioration is equal to or higher than a predetermined threshold, a caution message is displayed.

As understood from the explanation above, this disclosed example of the optical coherent tomography diagnostic apparatus is configured so that the standard light is split, in addition to the measuring light and the reference light, and the reference light and the standard light will exert interference on each other during the check mode.

The apparatus is constructed to manage the intensity of the coherent light between the reference light and the standard light. Consequently, it becomes possible for a user (doctor) to objectively recognize whether or not the amplification performance and the coherence performance of the light source and also the connection, the loss or the polarization state of the optical fiber are in good states.

The first exemplified embodiment of the optical coherent tomography diagnostic apparatus discussed above employs a construction in which the light path length of the standard light is equal to the light path length of the reference light. However, it is also possible to employ a construction in which in addition to this, a relation of "light path length of the standard light"<"light path length of the measuring light" or "light path length of measuring light+inspection range"<"light path length of the standard light" is first established and further, adjustment is executed by a one-axis stage 420 such that the light path length of the reference light will become equal to the light path length of the standard light.

In this manner, by virtue of the light path length of the standard light being largely different from the light path length of the measuring light, even if exerting interference of the standard light on the measuring light in the measurement mode, it does not happens that the influence appears in the measuring result (cross-sectional image). More specifically, it becomes unnecessary to make the shutter portion 432 a closing state during the measurement mode, so that the shutter portion 432 itself becomes unnecessary.

It should be noted that in this case, the one-axis stage 420 is operated such that the light path length of the reference light becomes equal to the light path length of the measuring light in the measurement mode and it happens that it is operated such that the light path length of the reference light becomes equal to the light path length of the standard light in a check mode.

In this manner, according to this embodiment described by way of example, even if there is no shutter portion 432, a similar effect as the first exemplified embodiment discussed above is obtained.

In the first embodiment described above by way of example, in a case in which it is judged that the amplification performance and the coherence performance of the light source, and also the connection, the loss or the polarization state of the optical fiber on the light path of the reference light are not in normal states, a configuration is employed for outputting a message of that fact. However, the apparatus is not limited only by this construction and it is also possible to employ a construction in which a polarization controller is arranged such that the polarization state of the reference light can be improved.

Figure 9:
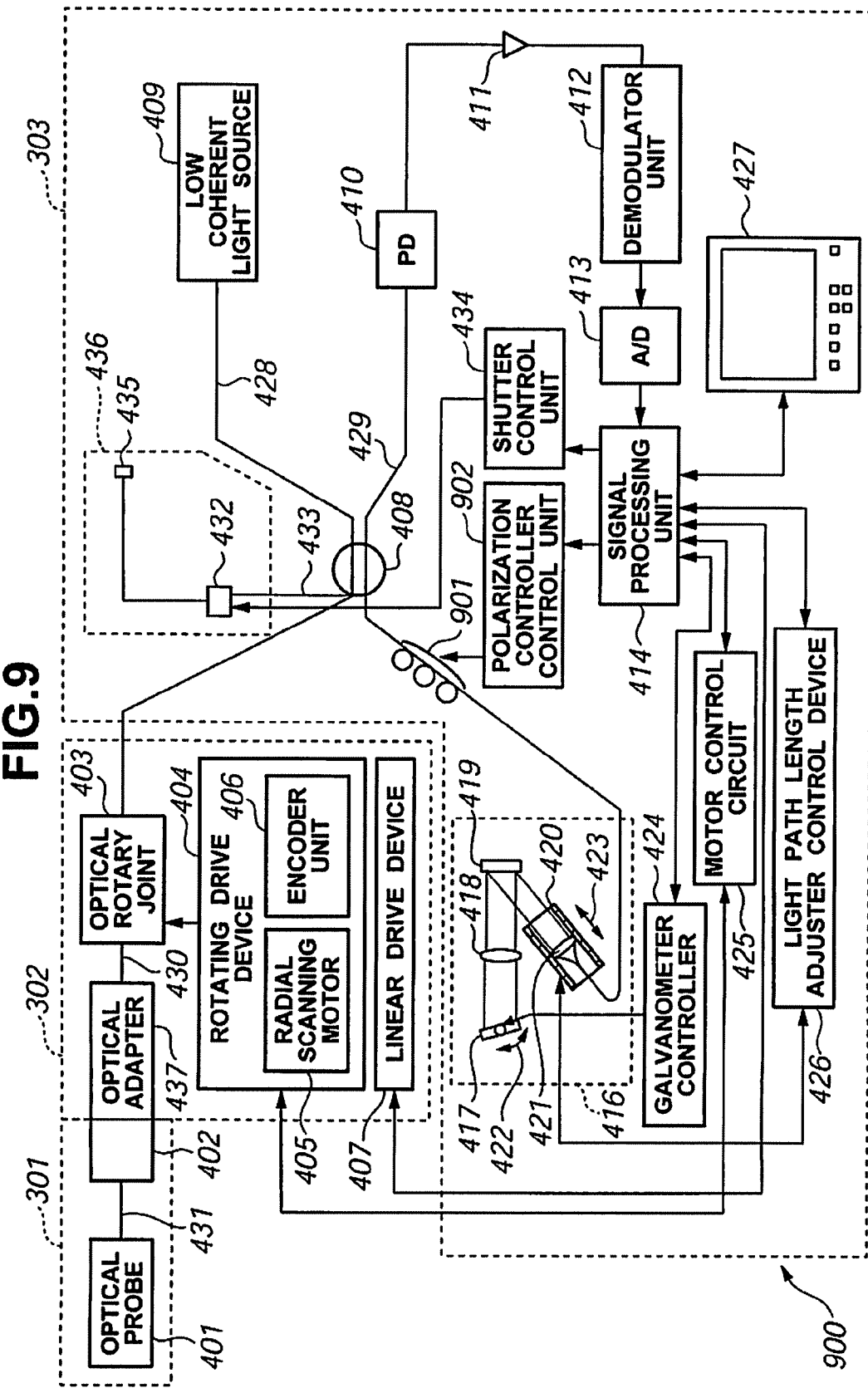
FIG. 9 is a schematic illustration of features of an optical coherent tomography diagnosis apparatus according to a second exemplified embodiment disclosed here.

FIG. 9 is a diagram showing features and characteristics of the optical coherent tomography diagnostic apparatus 900 according to another exemplified embodiment. As shown in FIG. 9, the optical coherent tomography diagnostic apparatus has a polarization controller 901. It is possible to improve the polarization state of the reference light by being operated under the control of a polarization controller control unit 902.

The polarization controller control unit 902 is connected with the signal processing unit 414. In the graph generating or producing unit 606, it is constituted such that an operation instruction is to be received from the signal processing unit 414 in a case in which it is judged that the polarization state of the optical fiber on the light path of the reference light is not normal.

In this manner, according to the present exemplified embodiment, even in a case in which the polarization state is not normal, it becomes possible to make an improvement without the need for the user (doctor) to call a service person.

The first to the third exemplified embodiments described above were discussed with respect to a case in which the disclosure is applied to an optical coherent tomography diagnosis apparatus. However, the disclosure here is not limited by the optical coherent tomography diagnostic apparatus and it is also possible to apply the diagnosis apparatus to a wavelength-sweeping optical coherent tomography diagnosis apparatus as discussed hereinafter.

1. Measurement Principle of Wavelength-Sweeping Optical Coherent Tomography Diagnosis Apparatus The measurement principle of a wavelength-sweeping optical coherent tomography diagnosis apparatus is generally as follows. The principle of the wavelength-sweeping optical coherent tomography diagnosis apparatus is basically the same as the measurement principle of the optical coherent tomography diagnosis apparatus explained in the first exemplified embodiment mentioned above, and illustrated in FIGS. 1 and 2, in the aspect utilizing the optical coherence. Consequently, the explanation which follows will center primarily around the points that differ with respect to the optical coherent tomography diagnosis apparatus.

A different point for the measurement principle with respect to the optical coherent tomography diagnosis apparatus lies in the light source and, first, the coherent length thereof is different. In other words, while the light source of the optical coherent tomography diagnosis apparatus uses a low coherent light having the coherent length of around 10 μm to 20 μm, the light source of the wavelength-sweeping optical coherent tomography diagnosis apparatus uses light having the coherent length of around 4 mm to 10 mm.

This is because, in the case of the wavelength-sweeping optical coherent tomography diagnosis apparatus, the inspection range in the depth direction of the biological tissue depends on the coherent length while, in case of the optical coherent tomography diagnosis apparatus, the inspection range in the depth direction of the biological tissue depends on the movable range of the reference mirror. In the wavelength-sweeping optical coherent tomography diagnosis apparatus, a light source having a comparatively long coherent length is used in order to fully cover the whole range in the depth direction of the biological tissue such as a blood vessel and the like.

A second different point of the light source is that light having different wavelengths are illuminated continuously by sweeping the wavelength continuously in the case of the wavelength-sweeping optical coherent tomography diagnosis apparatus.

In the optical coherent tomography diagnosis apparatus according to the first exemplified embodiment described above, the extraction of the reflection lights from respective points in the depth direction of the biological tissue is realized by the movement of the reference mirror, and the resolution in the depth direction of the subject of measurement depends on the coherent length of the light illuminated.

In contrast, in the case of the wavelength-sweeping optical coherent tomography diagnosis apparatus, a light whose wavelength is changed continuously is illuminated and the intensity of the reflection light from the respective points in the depth direction of the biological tissue is changed depending on the difference of the frequency component of the coherent light.

Generally, when considering the frequency (inverse of wavelength) of the light to be swept as a time function shown in the following formula (Formula 1), it is possible to express the intensity of the coherent light as a time function shown in the following formula (Formula 2). In this case, $\Delta x$ denotes the light path difference between the reference light and the measuring light, and $\Delta f$ denotes the rate of frequency change in a unit time period (A, B, C indicate constant values).

$$f(t)=f\alpha+\Delta ft \quad \text{(Formula 1)}$$

$$I(t)=A+B\cos(C\Delta x(f\alpha+\Delta ft)) \quad \text{(Formula 2)}$$

As known from the Formula 2, the frequency component of the time period change of the coherent light intensity $I(t)$ is expressed by the light path difference $\Delta x$ and the frequency change $\Delta f$ of the wavelength-sweeping. Consequently, knowing the frequency component of the coherent light, the coherent light intensity for every light path difference is to be known.

Thus, a time period required for obtaining a signal for one line becomes short and also, it is possible to widen the detection range in the depth direction.

Figure 10:
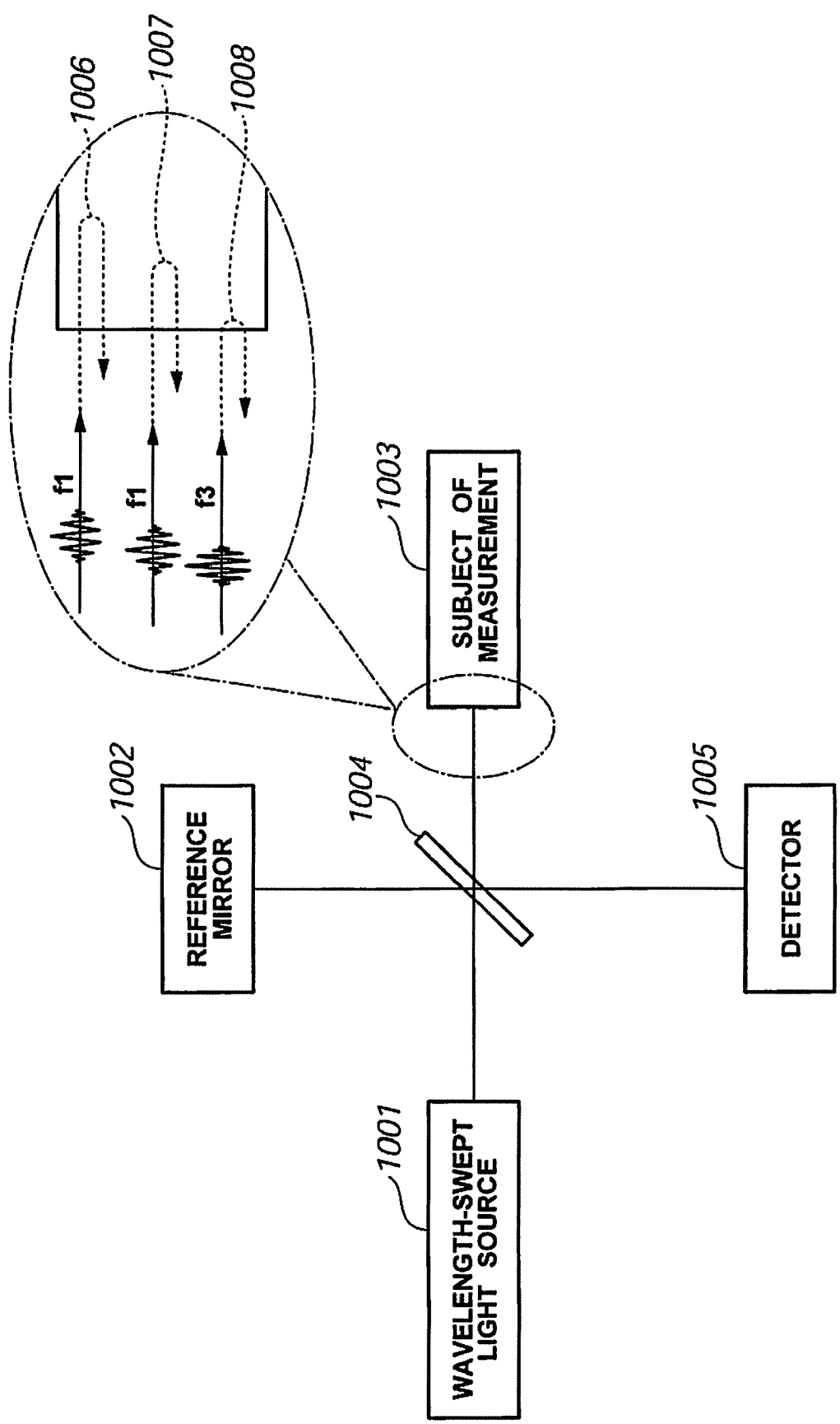
FIG. 10 is a schematic illustration of the basic principle of a wavelength-sweeping optical coherent tomography diagnostic apparatus.

FIG. 10 is a diagram showing the basic principle wavelength-sweeping optical coherent tomography diagnosis apparatus. In the same drawing, a wavelength-swept light source 1001 is a Swept Laser.

The lights including different frequencies, which are outputted sequentially from the wavelength-swept light source 1001, are split by a beam splitter 1004 and respective lights are directed to a reference mirror 1002 and a subject of measurement 1003. The reflection light returned from the subject of measurement 1003 side at that time includes reflection lights from various positions such as, for example, a reflection light reflected on the material body surface, a light reflected at a shallow position inside the material body, and a light reflected at a deep portion inside the material body.

As mentioned above, it becomes possible, in a detector 1005, to make structural information at a specified position in the depth direction of the subject of measurement visible by frequency-resolving the observed coherent light. As a result, it is possible to form a tomographic image.

The light outputted from the wavelength-swept light source 1001 has a coherent length of around 4 to 10 mm and therefore, the whole inspection range in the depth direction of the subject of measurement can be fully covered. It thus happens that the reference mirror does not need to be operated and the reference mirror 1002 is to be arranged fixedly at a fixed distance.

In this manner, it is not necessary to move the reference mirror mechanically, so that in case of a wavelength-sweeping optical coherent tomography diagnosis apparatus, the time period required for obtaining a signal for one line becomes short as compared with the optical coherent tomography diagnosis apparatus and it is possible to raise the frame rate thereof. While the maximum frame rate in the optical coherent tomography diagnosis apparatus is 15 fr/s, the frame rate of the wavelength-sweeping optical coherent tomography diagnosis apparatus is around 30 to 200 fr/s.

Primarily, in case of an optical coherent tomography diagnosis apparatus or a wavelength-sweeping optical coherent tomography diagnosis apparatus, the blood must be removed on an occasion of a diagnosis in order to avoid absorption of the light to a blood-cell component and in order to obtain a good cross-section image. For this reason, the time period in which the blood is removed must be made relatively long if the frame rate is low and it is not preferable clinically. On the contrary, in the case of a wavelength-sweeping optical coherent tomography diagnosis apparatus, it is possible to obtain a cross-sectional image of 30 mm or more in the axial direction of the blood vessel upon blood removal for a few seconds, so that there is a merit that the clinical problem can be lowered.

Figure 11:
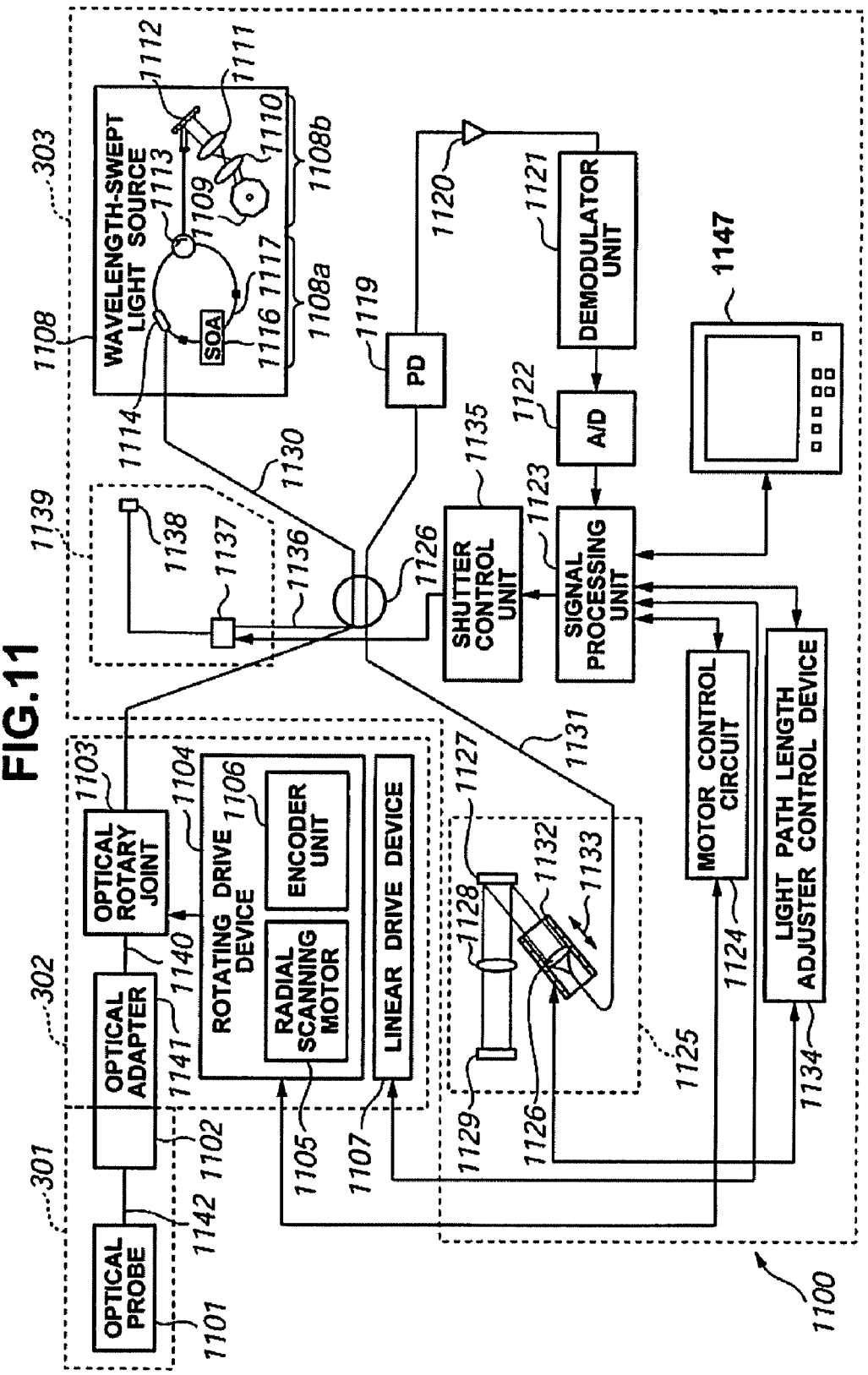
FIG. 11 is a schematic illustration of features of a wavelength-sweeping optical coherent tomography diagnostic apparatus.

2. Features of Wavelength-Sweeping Optical Coherent Tomography Diagnosis Apparatus FIG. 11 illustrates features of the wavelength-sweeping optical coherent tomography diagnosis apparatus 1100. The description below will primarily center around differences with respect to the optical coherent tomography diagnosis apparatus which was explained with referenced to FIG. 4 in the first exemplified embodiment discussed above. Features associated with this wavelength-sweeping optical coherent tomography diagnosis apparatus 1100 that are the same as those previously described are illustrated in a corresponding manner and are not discussed below in detail.

As shown in FIG. 11, a wavelength-swept light source 1108 using a Swept Laser is used. The wavelength-swept light source 1108 using the Swept Laser is a kind of Extended-cavity Laser composed of a SOA 1116 (semiconductor optical amplifier), an optical fiber 1117 coupled in a ring shape, and a polygon scanning filter 1108b.

The light outputted from the SOA 1116 proceeds to the optical fiber 1117 and enters into the polygon scanning filter 1108b, in which the light whose wavelength is selected is here amplified in the SOA 1116 and finally outputted from the coupler 1114.

The polygon scanning filter 1108b selects the wavelength in combination of a diffractive grating 1112 for spectrally diffracting the light and a polygon mirror 1109. The light spectrally diffracted by the diffractive grating 1112 is focused on the surface of the polygon mirror 1109 by two lenses or lens pieces 1110, 1111. Thus, only the light of the wavelength which is perpendicular to the polygon mirror 1109 returns in the same light path and is outputted from the polygon scanning filter 1108b, so that it is possible to execute the time sweeping of the wavelength by rotating the mirror.

For the polygon mirror 1109, for example, a thirty-two polyhedral mirror is used and the rotational speed thereof is around 50000 rpm. According to a unique wavelength sweeping system formed by a combination of the polygon mirror 1109 and the diffractive grating 1112, it is possible to employ wavelength-sweeping of high-speed and of high-power output.

The light of the wavelength-swept light source 1108 outputted from the coupler 1114 enters one end of a first single-mode fiber 1130 and is transmitted to the distal surface side thereof. The first single-mode fiber 1130 is coupled optically with a second single-mode fiber 1131 and a third single-mode fiber 1136 at an optical coupler unit 1126. Consequently, the light is transmitted by being split into three light paths at the maximum owing to this optical coupler portion 1126.

On the distal side (in the measuring light path) from the optical coupler portion 1126 of the first single-mode fiber 1130, an optical rotary joint 1103 is provided for attaining coupling between a non-rotating portion and a rotating portion and for transmitting the light.

Further, at the distal side of a fourth single-mode fiber 1140 in the optical rotary joint 1103, a connector portion 1102 of the catheter unit 301 is detachably connected with respect to an optical adapter unit 1141 of the scanner/pullback unit 302. Thus, the light is transmitted from the wavelength-swept light source 1108 to a fifth single-mode fiber 1142 which is inserted into or positioned in an optical probe 1101 and which is rotatingly drivable.

The transmitted light is illuminated while being scanned radially from the distal side of the optical probe 1101 to the biological tissue in the coelom. Then, a portion of the reflection lights diffused on the surface or in the inside of the biological tissue is taken-in by the optical probe 1101 and returns to the first single-mode fiber 1130 side via a reverse light path. Further, a portion thereof is shifted to the second single-mode fiber 1131 side by the optical coupler unit 1126 and emanates from one end of the second single-mode fiber 1131 and is received by a photodetector (for example, photodiode 1119). The rotation unit side of the optical rotary joint 1103 is driven rotatingly by a radial scanning motor 1105 of a rotating drive device 1104. Also, the rotation angle of the radial scanning motor 1105 is detected by an encoder unit 1106. Further, the scanner/pullback unit 302 includes a linear drive device 1107 and defines the operation of the insertion direction of the catheter unit 301 based on the instruction from the signal processing unit 1123.

On the distal side (in reference to the light path) of the second single-mode fiber 1131 of the second single-mode fiber 1131 from the optical coupler unit 1126, there is provided a variable mechanism 1125 of a light path length for fine-adjusting the light path length of the reference light.

The variable mechanism 1125 of this light path length includes a light-path length changer for changing a light path length corresponding to fluctuation of the lengths thereof so as to absorb the fluctuation of the lengths of individual optical probes in case of using optical probes exchangingly.

The second single-mode fiber 1131 and a collimating lens are provided on one axis stage 1132 which is freely movable in the light axial direction thereof as shown by an arrow 1133, and a light-path length changer is formed.

More specifically, in the case of exchanging the optical probe 1101, the one axis stage 1132 functions as a second light-path length changer having a variable range of the light path length such that the fluctuation of the light path length of the optical probe can be absorbed. Further, the one axis stage 1132 functions also as an adjuster for adjusting offset. For example, even in a case in which the distal tip of the optical probe 1101 is not closely-attached (located) on the surface of the biological tissue, it becomes possible, by changing the light path length in a relatively minute manner depending on the one axis stage 420, to set a state of exerting interference to the reflection light from the surface position of the biological tissue.

The light which was fine-adjusted for the light path length by the variable mechanism 1125 of the light path length is mixed with the light obtained from the first single-mode fiber 1130 side in the optical coupler unit 1126 provided on the way of the second single-mode fiber 1131 and is light-received by the photodiode 1119.

On the distal side of the third single-mode fiber 1136 (with reference to the standard light path), a standard light transmission mechanism 1139 is provided for transmitting the standard light used to confirm the amplification performance and the coherence performance of the light source, and also the connection, the loss or the polarization state of the optical fiber (second single-mode fiber 1131) forming the light path of the reference light.

The standard light transmission mechanism 1139 is constructed such that the standard light split at the optical coupler portion 1126 is reflected on a reflection mirror 1138 and thereafter, the light path length until exerting interference with the reference light becomes equal to the light path length of the reference light in the optical coupler portion 1126.

In the light path of the standard light, there is disposed a shutter portion 1137, and a shutter control unit 1135 executes control of an open/close operation of the shutter portion based on an open/close instruction from the signal processing unit 1123. The shutter portion 1137 is in a closing state in a case in which the catheter unit 301 is connected to the scanner/pull-back unit 302 and forms a cross-sectional image of the biological tissue (in case of measurement mode). On the other hand, the shutter portion 1137 is in an open state in a case in which the connection of the catheter unit 301 is disconnected and the connection, the loss or the polarization state of the optical fiber (second single-mode fiber 1131) forming the amplification performance and the coherence performance of the light source, and the light path of the reference light is confirmed (in case of check mode).

The standard light reflected on the reflection mirror 1138 in the inside of the standard light transmission mechanism 1139 is to be mixed with the light obtained from the second single-mode fiber 1131 side at the optical coupler portion 1126 and is light-received by the photodiode 1119 as a coherent light.

The standard light transmission mechanism 1139, when transmitting the standard light, does not have a connection portion on the light path and does not have such a movable portion which changes the light path length either. Consequently, there is little deterioration of the standard light caused by bad connection, and the intensity or the coherence performance of the standard light is not significantly lowered.

In this manner, the coherent light (coherent light of measuring light and reference light in the case of the measurement mode, and coherent light of standard light and reference light in the case of the check mode) received by the photodiode 1119 is converted photoelectrically, is amplified by an amplifier 1120 and thereafter, is inputted to a demodulator unit 1121. A demodulation process is performed in this demodulator unit 1121 for extracting only a signal component of the coherent light and the output thereof is inputted to an A/D converter 1122 as a coherent light signal.

In the A/D converter 1122, digital data of one line (coherent light data) is generated by sampling the coherent light signal with 180 MHz for 2048 points. Here, the selection of the sampling frequency to be 180 MHz is caused by an assumption that around 90% of the period (12.5 μsec) of the wavelength-sweeping is extracted as digital data of 2048 points in the case of assuming that the repetition frequency of the wavelength-sweeping is 40 kHz, though the apparatus here is not limited by this fact particularly.

The coherent light data of a line unit which is generated in the A/D converter 1122 is inputted to the signal processing unit 1123. In the case of a measurement mode, in the signal processing unit 1123, data in the depth direction is generated by frequency-resolving the coherent light data using FFT (Fast Fourier Transform) and by coordinate-converting this, and tomographic images at respective positions in the blood vessel are formed and outputted by a predetermined frame rate to an LCD monitor 1147.

On the other hand, in case of a check mode, the time change of the coherent light data is calculated in the signal processing unit 1123 and this is graph-displayed on the LCD monitor 1147. At the same time, it is judged whether or not the amplification performance and the coherence performance of the light source, and also the connection, the loss or the polarization state of the optical fiber forming the light path of the reference light are in normal states.

Thus, it is possible for the user to recognize objectively whether or not the amplification performance and the coherence performance of the light source, and also the connection, the loss or the polarization state of the optical fiber are in good states.

The signal processing unit 1123 is further connected with a light path length adjuster control device 1134. The signal processing unit 1123 carries out position control of the one axis stage 1132 through the light path length adjuster control device 1134. Also, the signal processing unit 1123 is connected with a motor control circuit 1124 and stores the tomographic image in an internal memory in synchronization with the video synchronous signal when forming the tomographic image.

In addition, the video synchronous signal of this motor control circuit 1124 is also transmitted to the rotating drive device 1104 and the rotating drive device 1104 outputs a drive signal in synchronism with the video synchronous signal.

3. Light Transmission Path in Wavelength-Sweeping Optical Coherent Tomography Diagnostic Apparatus The following describes an outline of transmission paths until the light is received by the photodiode 1119 after the light outputted from the wavelength-swept light source 1108 is split and transmitted on the respective light paths in the wavelength-sweeping optical coherent tomography diagnostic apparatus 1100.

Figure 12:
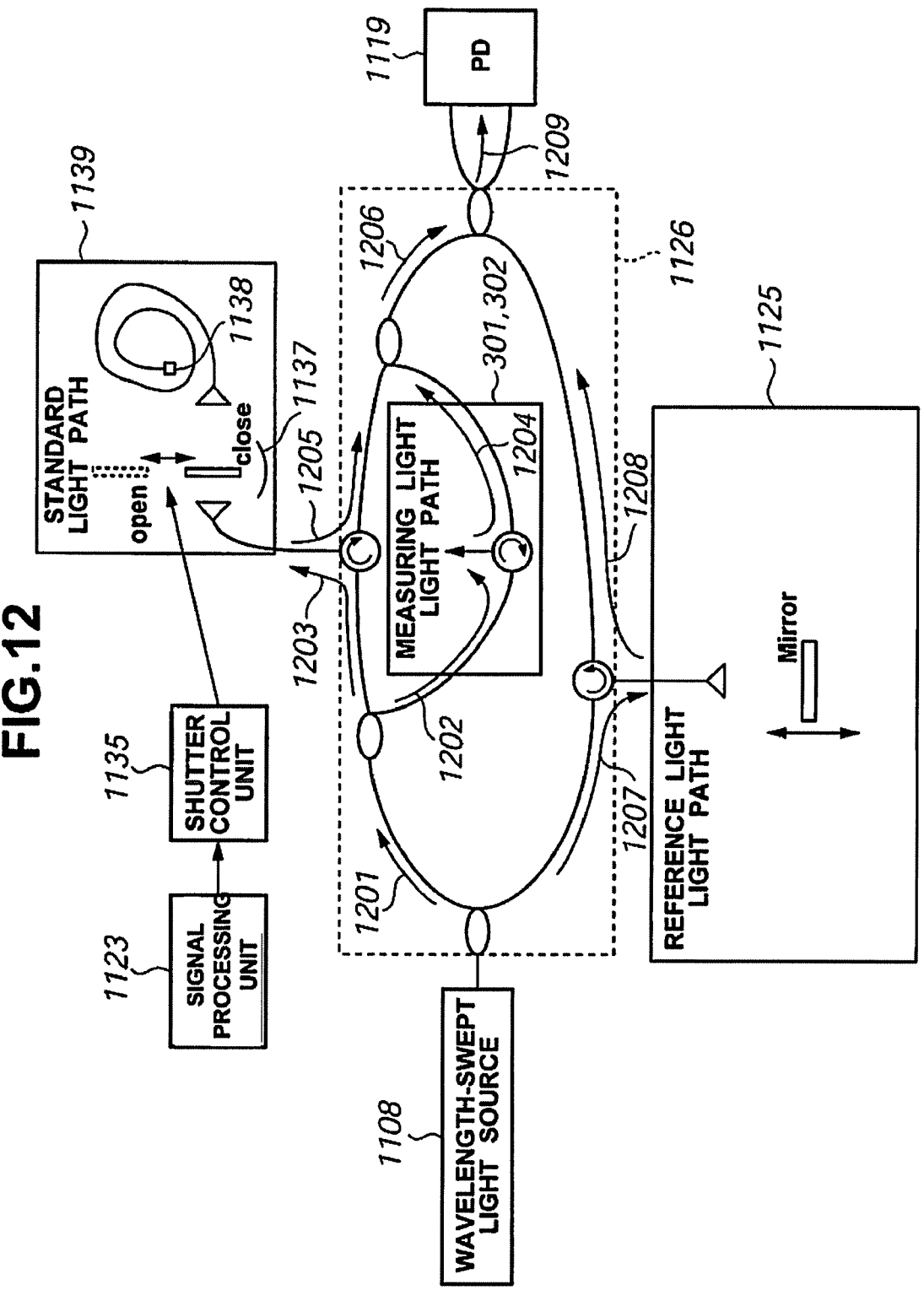
FIG. 12 is a schematic illustration of a transmission path in the optical coherent tomography diagnostic apparatus.

FIG. 12 schematically shows transmission paths in the wavelength-sweeping optical coherent tomography diagnostic apparatus 1100 relating to the present exemplified embodiment. As shown in FIG. 12, the light outputted from the wavelength-swept light source 1108 is inputted to the optical coupler portion 1126.

Then, in case of a measurement mode, the measuring light is transmitted as 1201→1202→1204→1206, is to be mixed with the reference light transmitted as 1207→1208 and exerts interference therewith. The coherent light is transmitted in the direction of the arrow 1209 and is light-received in the photodiode 1119.

On the other hand, in case of a check mode, the standard light is transmitted as 1201→1203→1205→1206, is to be mixed with the reference light transmitted as 1207→1208 and exerts interference therewith. The coherent light is transmitted in the arrow 1209 direction and is light-received in the photodiode 1119.

4. Detailed Constitution of Signal Processing Unit 1123

Figure 13:
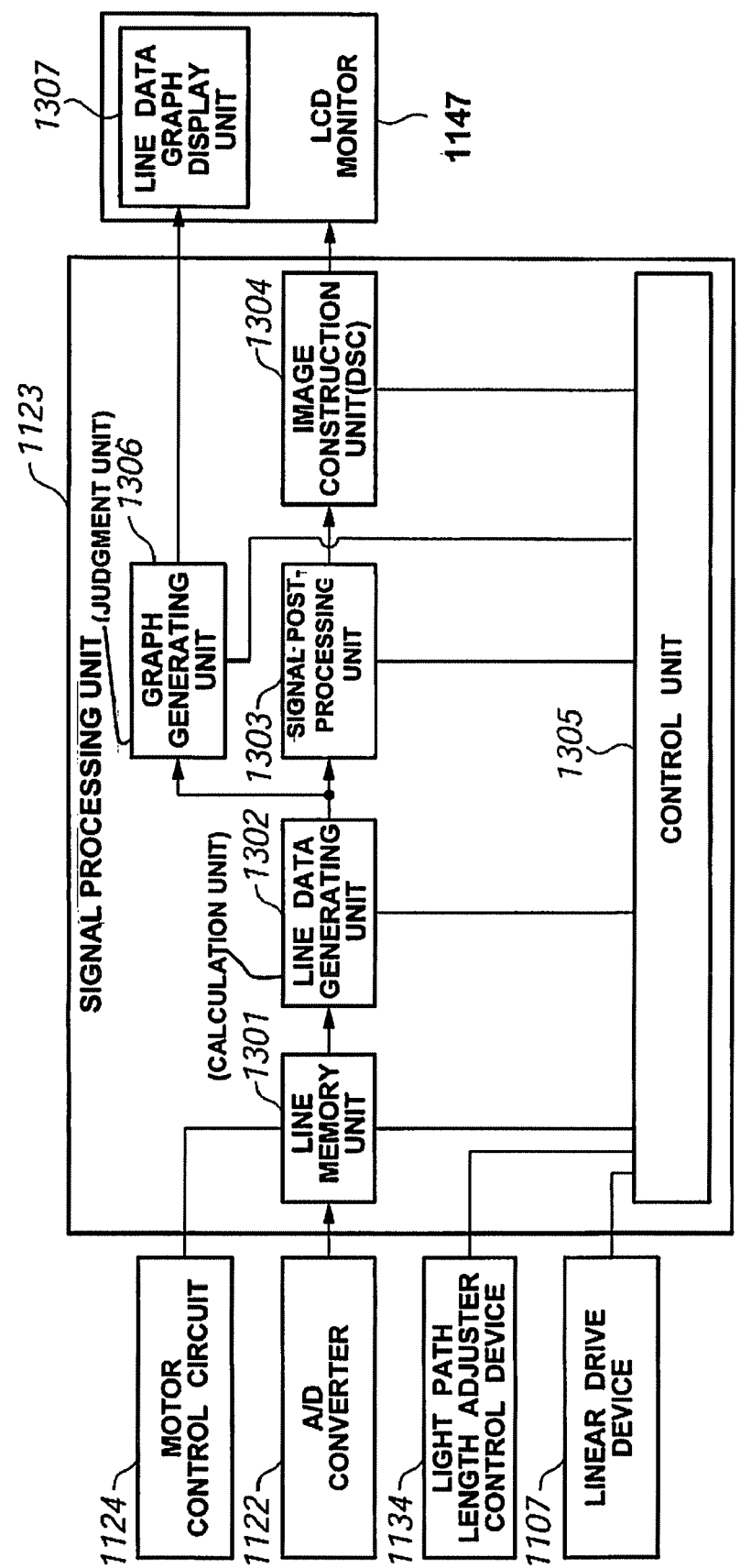
FIG. 13 is a schematic illustration of aspects of the signal processing unit generally illustrated in FIG. 12 and related function block.

Referring to FIG. 13, the following is a description of outlining a process in the signal processing unit 1123 of the wavelength-sweeping optical coherent tomographic apparatus 1100. In the case of a measurement mode, the coherent light data generated in the A/D converter 1122 is processed such that the number of lines per one rotation of the radial scanning motor becomes 515 lines by using the signal of the encoder unit 1106 of the radial scanning motor 1105 outputted from the motor control circuit 1124 in a line memory unit 1301 and thereafter, is outputted to a line data generating unit 1302 of a succeeding stage.

In the line data generating unit 1302, which is an example of a calculation unit which calculates the time change of coherent light data obtained by exerting interference between the standard light and the reference light, the coherent light data is frequency-resolved by the FFT and line data are generated by generating coherent light intensity data in the depth direction of the biological tissue. Thereafter, the generated line data are outputted to a signal post-processing unit 1303 of a succeeding stage. In the signal post-processing unit 1303, various processes such as a contrast adjustment, a luminance adjustment, a gamma correction, a frame correlation processing, and a sharpness processing are applied with respect to the line data in which it is outputted to an image construction unit (DSC) 1304.

In the image construction unit 1304, it is converted to a video signal from the line data sequence of the polar coordinate and a cross-sectional image is displayed on the LCD monitor 1147. It should be noted here that an embodiment in which an image is constituted from 512 lines is shown as one example, but the apparatus disclosed here it is not limited by only this number of lines.

On the other hand, in a check mode, the coherent light data generated in the A/D converter 1122 is stored in the line memory unit 1301 with the data amount necessary for the graph display and thereafter, the data are outputted to the line data generating unit 1302 in the succeeding stage.

In the line data generating unit 1302, the coherent light data is frequency-resolved by the FFT and the line data is generated by generating the coherent light intensity data in the depth direction of the biological tissue and thereafter, the data is outputted to a graph generating or producing unit 1306 in a succeeding stage. Like the graph generating unit 606 described above, the graph generating unit 1306 is an example of a judgment unit for judging the state of the light path for transmitting the reference light based on the coherent light intensity.

In the graph producing or generating unit 1306, the maximum value of the coherent light intensity is detected based on the inputted coherent light data. Also, attenuation from the maximum value in the depth direction of the coherent light intensity (that is, with respect to the light path length difference) is compared with a predetermined base attenuation and it is judged whether or not the attenuation is equal to or higher than the base attenuation. Details of the processing in the graph generating unit 1306 will be explained later.

In a coherent light data graph display unit 1307, there is such a control so as to display a graph in the depth direction of the coherent light data on the LCD monitor 1147 and at same time, there are displayed, for example, the maximum value of the coherent light intensity calculated in the graph producing unit 1306, the attenuation from the maximum value in the depth direction, and the base attenuation which is used for the calculation.

5. Detail of Processing in Graph Generating Unit 1306

Figure 14:
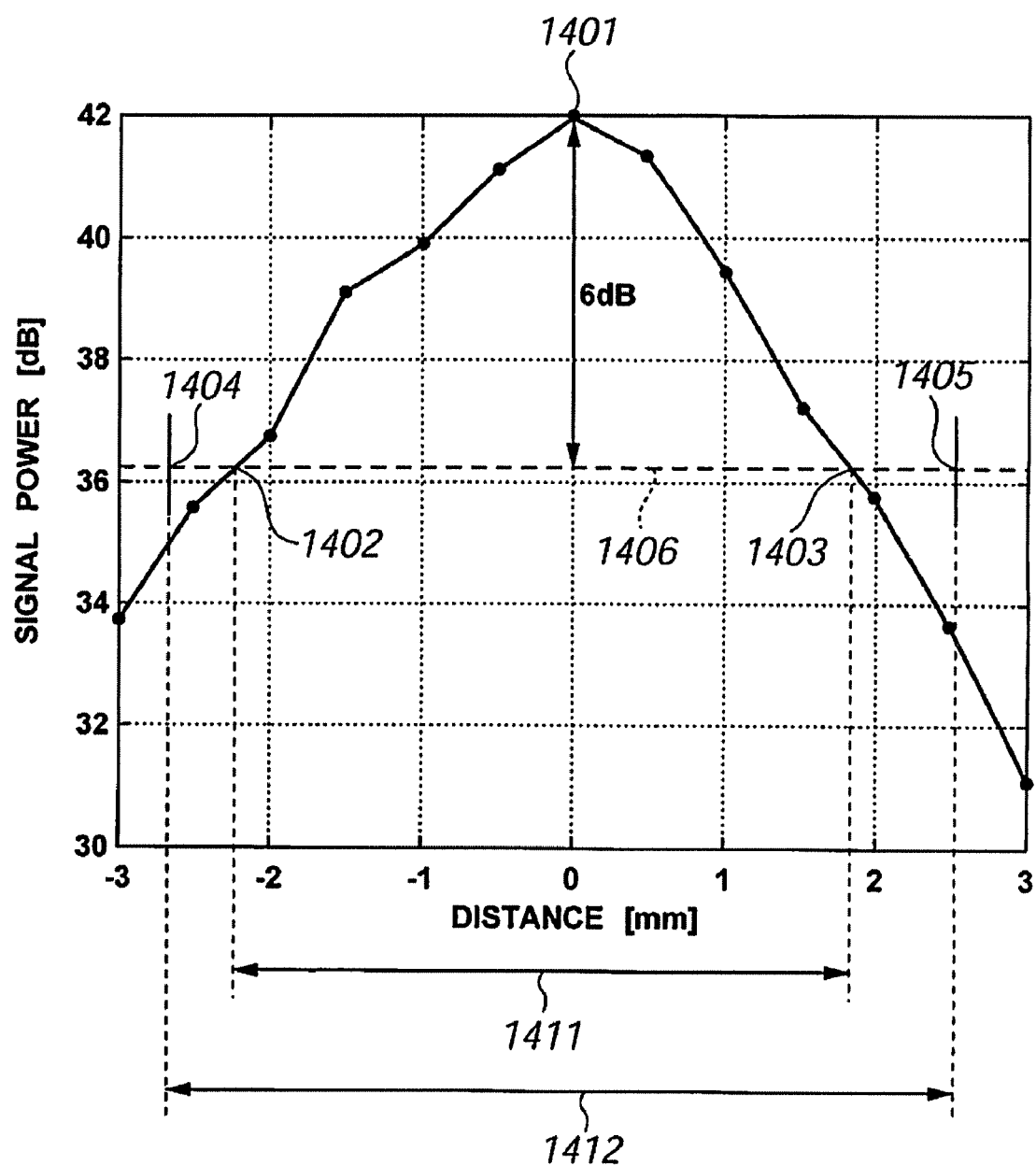
FIG. 14 is an example of a graph produced based on coherent light data inputted to the graph generating unit shown in FIG. 13.

FIG. 14 illustrates details associated with the processing in the graph generating unit 1306. In FIG. 14, the horizontal axis denotes distance in the depth direction and the vertical axis denotes intensity of the coherent light data. As shown in FIG. 14, in case of the wavelength-sweeping optical coherent tomography diagnostic apparatus, the intensity of the coherent light data becomes maximum at the position in which the light path lengths of the standard light and the reference light are equal (position in which the difference between the light path length of the standard light and the light path length of the reference light is equal to zero), and the larger the amount of deviation from there becomes, the more the intensity of the coherent light data attenuates.

Then, in the wavelength-sweeping optical coherent tomography diagnostic apparatus 1100, it is judged based on this degree of attenuation whether or not the amplification performance of the light source, the existence/non-existence of deterioration of the coherence performance, and the connection, the loss or the polarization state of the optical fiber are in good states.

Consequently, in the graph generating unit 1306, first, based on the inputted line data, there is calculated the change of the intensity of the coherent light data with respect to the amount of deviation (distance) from the position in which the light path lengths of the standard light and the reference light are equal and at the same time, the maximum value 1401 of the intensity of the coherent light data is detected.

Further, a point in which the intensity of the coherent light data is attenuated by a predetermined value (here, 6 dB) seen from the maximum value 1401 is extracted. As mentioned above, in case of the wavelength-sweeping optical coherent tomography diagnostic apparatus, the coherent light data become maximum at the position in which the difference between the light path length of the standard light and the light path length of the reference light is zero, so that there exist two points (1402, 1403) whose attenuation is a predetermined value seen from the maximum value 1401. Then, the distance (attenuation distance) 1411 between the extracted two points is calculated.

Further, in the graph generating unit 1306, the distance 1411 is compared with a predetermined standard distance 1412 (distance which should be owned by coherent light obtained by exerting interference between reference light and standard light transmitted in the light path recognized as normal, and distance between the points 1404 and 1405). Then, it is judged whether or not a condition of "attenuation distance"≦"standard distance" is true (whether or not a condition equal to or higher than the standard attenuation is established).

Further, in a case in which a condition of "attenuation distance"≦"standard distance" is true, it is judged that the amplification performance and the coherence performance of the light source, and the connection, the loss or the polarization state of the optical fiber on the light path of the reference light are not normal, and a message of that fact is outputted.

Figure 15:
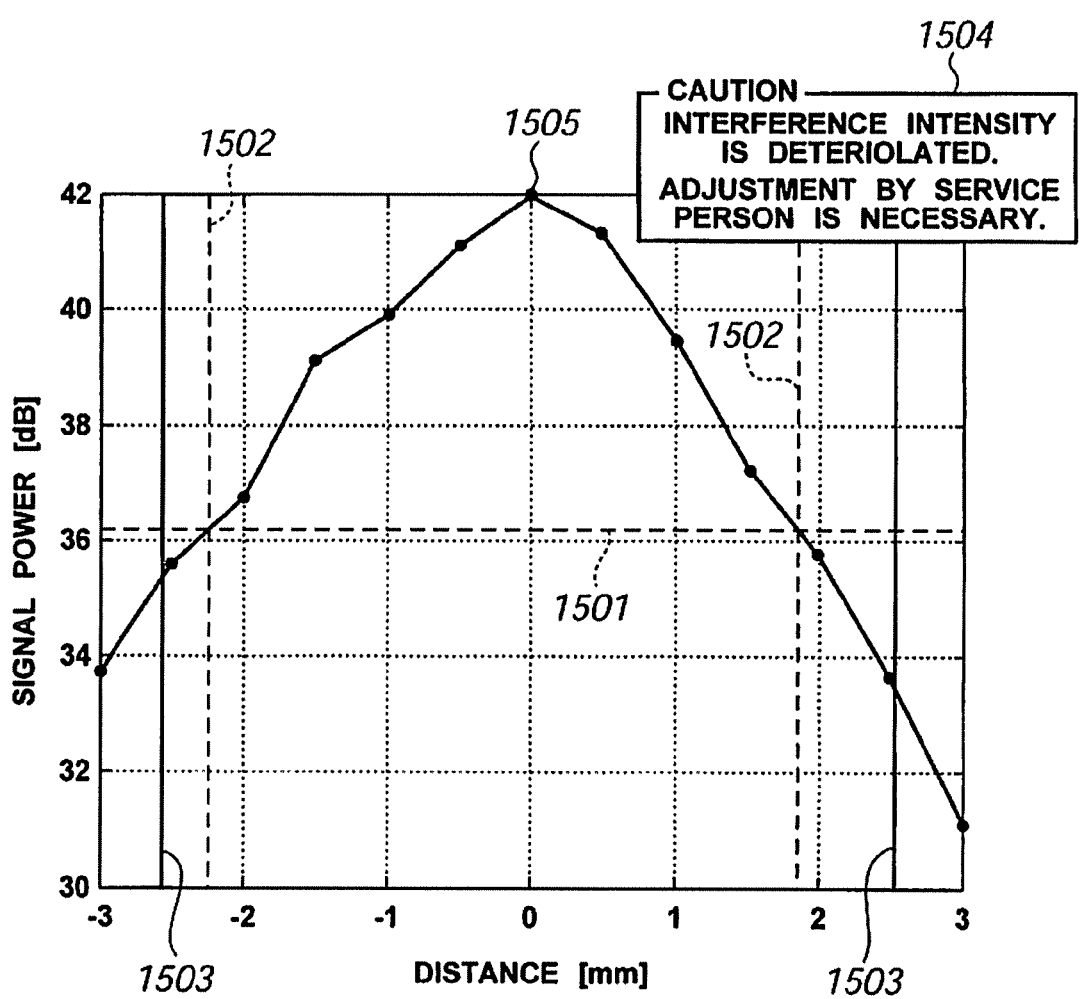
FIG. 15 is an example of graph-displayed coherent light data processed in the graph generating unit shown in FIG. 13.

FIG. 15 is a diagram showing an aspect in which coherent light data processed in the graph generating unit 1306 is graph-displayed.

As shown in FIG. 15, a dotted line 1501 is displayed at the position attenuated by 6 dB from the maximum value 1505 and at the same time, a dotted line 1502 is displayed at a cross point between the dotted line 1501 and the coherent light data in order to show the attenuation distance. Further, a solid line 1503 is displayed in order to show the standard distance.

Further, a caution message 1504 is displayed in a case in which a condition of "attenuation distance"≦"standard distance" is true.

As being clear from the explanation above, a configuration is employed in the wavelength-sweeping optical coherent tomography diagnostic apparatus relating to the present exemplified embodiment in which the standard light is split other than the measuring light and the reference light, and the reference light and the standard light will exert interference on each other.

Then, it was designed to manage the degree of attenuation in the depth direction of the intensity of the coherent light between the reference light and the standard light. Consequently, it becomes possible for a user (doctor) to objectively recognize whether or not the amplification performance and the coherence performance of the light source and also the connection, the loss or the polarization state of the optical fiber are in good states.

The fourth exemplified embodiment discussed above employs a construction in which the light path length of the standard light becomes equal to the light path length of the reference light. However, it is also possible to employ a construction in which, in addition to this, a relation of "light path length of the standard light"<"light path length of the measuring light" or "light path length of measuring light+inspection range"<"light path length of the standard light" is first established and further, adjustment is executed by a one-axis stage 1132 such that the light path length of the reference light will become equal to the light path length of the standard light.

In this manner, by constituting the light path length of the standard light so as to become largely different from the light path length of the measuring light, even if exerting interference of the standard light on the measuring light in the measurement mode, it never happens that the influence appears in the measuring result (cross-section image). More specifically, there becomes unnecessary to make the shutter portion 1137 as a closing state during the measurement mode, so that the shutter portion 1137 itself becomes unnecessary.

It should be noted that in this case, the one-axis stage 1132 is operated such that the light path length of the reference light becomes equal to the light path length of the measuring light in the measurement mode and it happens that it is operated such that the light path length of the reference light becomes equal to the light path length of the standard light in a check mode.

In this manner, according to the present exemplified embodiment, even if there is no shutter portion 1137, a similar effect as the fourth exemplified embodiment mentioned above is obtained.

In the fourth exemplified embodiment mentioned above, in a case in which it is judged that the amplification performance and the coherence performance of the light source, and also the connection, the loss or the polarization state of the optical fiber on the light path of the reference light are not in normal states, there is employed a configuration for outputting a message of that fact, but the apparatus here is not limited only by this. It is also possible to employ a construction in which a polarization controller is arranged such that the polarization state of the reference light can be improved.

Figure 16:
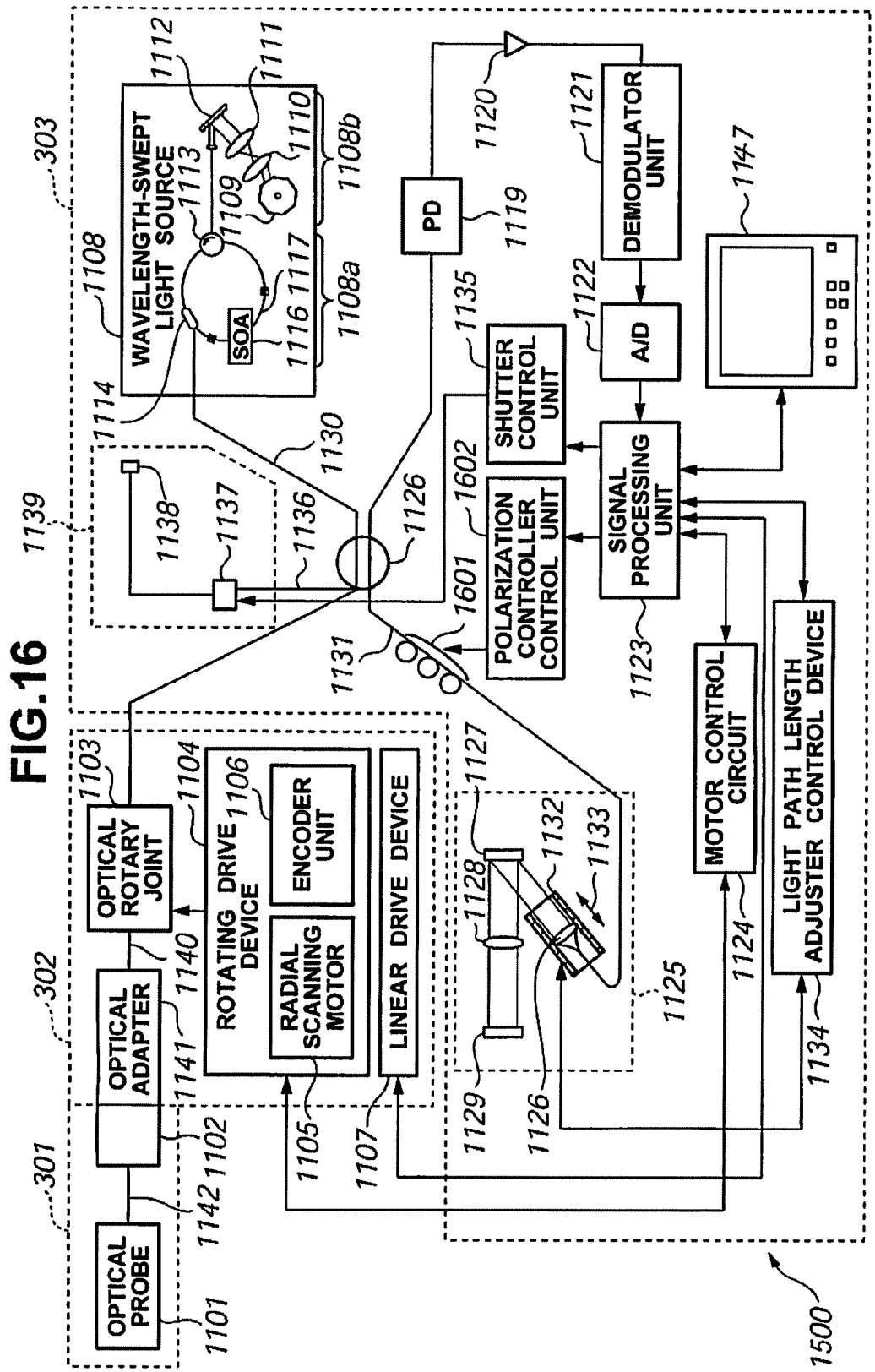
FIG. 16 is a schematic illustration of features of an optical coherent tomography diagnosis apparatus according to a further exemplified embodiment disclosed here.

FIG. 16 is a diagram showing features of the optical coherent tomography diagnostic apparatus 1600 relating to the present exemplified embodiment. As shown in FIG. 16, the optical coherent tomography diagnostic apparatus relating to the present exemplified embodiment has a polarization controller 1601 and it is possible to improve the polarization state of the reference light by being operated under the control of a polarization controller control unit 1602.

It should be noted that the polarization controller control unit 1602 is connected with the signal processing unit 1123 and in the graph producing unit 1306, it is constituted such that an operation instruction is to be received from the signal processing unit 1123 in a case in which it is judged that the polarization state of the optical fiber on the light path of the reference light is not normal.

In this manner, according to the present exemplified embodiment, even in a case in which the polarization state is not normal, it becomes possible to make an improvement without calling a service person by a user (doctor).

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. An optical coherent tomography diagnostic apparatus comprising:
   a light source for outputting light;
   a splitter for splitting the light outputted from the light source into a measuring light, a reference light, and a standard light;
   a measuring light path connected to the splitter to transmit the measuring light;
   a reference light path connected to the splitter to transmit the reference light;
   a standard light path connected to the splitter to transmit the standard light;
   a probe insertable into a body cavity, the probe being connected to the measuring light path to emit the measuring light to a subject of measurement, with light being reflected from the subject of measurement as reflection light;
   an image forming unit for calculating intensity distribution of the reflection light in an emission direction of the measuring light and for forming a tomographic image of the subject of measurement based on the intensity distribution by rendering the reflection light from the subject of measurement, which was obtained by the probe to have interference with the reference light;
   a light path length when exerting interference between the standard light and the reference light is approximately equal to a light path length when exerting interference between the reference light and the reflection light; and
   a calculation unit which calculates time change of coherent light data obtained by exerting interference between the standard light and the reference light;
   wherein the standard light path does not have a movable portion for varying the light path length.

2. The optical coherent tomography diagnostic apparatus according to claim 1, wherein the standard light path is formed as an optical fiber without a connection portion.

3. The optical coherent tomography diagnostic apparatus according to claim 1, wherein the light path length of the standard light path is different from the light path length until the measuring light exerts interference on the reference light as the reflection light.

4. The optical coherent tomography diagnostic apparatus according to claim 1, wherein the light source is a low coherent light source.

5. The optical coherent tomography diagnostic apparatus according to claim 1, wherein the light source is a wavelength-swept light source.

6. The optical coherent tomography diagnostic apparatus according to claim 4, wherein coherent light intensity is obtained based on the time change of the coherent light data calculated by the calculation unit, and further comprising a judgment unit for judging a state of the light path for transmitting the reference light based on the coherent light intensity.

7. The optical coherent tomography diagnostic apparatus according to claim 6, wherein the judgment unit judges that the state of the light path for transmitting the reference light is not normal when a degree of deterioration of the coherent light intensity with respect to a predetermined reference intensity exceeds a predetermined threshold.

8. An optical coherent tomography diagnostic apparatus comprising:
   a light source for outputting light, the light source being a wavelength-swept light source;
   a splitter for splitting the light outputted from the light source into a measuring light, a reference light, and a standard light;
   a measuring light path connected to the splitter to transmit the measuring light;
   a reference light path connected to the splitter to transmit the reference light;
   a standard light path connected to the splitter to transmit the standard light;
   a probe insertable into a body cavity, the probe being connected to the measuring light path to emit the measuring light to a subject of measurement, with light being reflected from the subject of measurement as reflection light;
   an image forming unit for calculating intensity distribution of the reflection light in an emission direction of the measuring light and for forming a tomographic image of the subject of measurement based on the intensity distribution by rendering the reflection light from the subject of measurement, which was obtained by the probe to have interference with the reference light;
   a light path length when exerting interference between the standard light and the reference light is approximately equal to a light path length when exerting interference between the reference light and the reflection light; and
   a calculation unit which calculates time change of coherent light data obtained by exerting interference between the standard light and the reference light;
   wherein based on the time change of the coherent light data calculated by the calculation unit, a degree of attenuation of the intensity of the coherent light data with respect to the amount of deviation from a position at which the light path lengths of the standard light and the reference light are equal is obtained, and further comprising a judgment unit for judging a state of the light path for transmitting the reference light based on the degree of attenuation.

9. The optical coherent tomography diagnostic apparatus according to claim 8, wherein the judgment unit judges that the state of the light path for transmitting the reference light is not normal in a case in which the degree of attenuation exceeds a predetermined reference value.

10. An optical coherent tomography diagnostic apparatus comprising:
    a light source for outputting light;
    a splitter for splitting the light outputted from the light source into a measuring light, a reference light, and a standard light;
    a measuring light path connected to the splitter to transmit the measuring light;
    a reference light path connected to the splitter to transmit the reference light;
    a standard light path connected to the splitter to transmit the standard light;
    a probe insertable into a body cavity, the probe being connected to the measuring light path to emit the measuring light to a subject of measurement, with light being reflected from the subject of measurement as reflection light;
    an image forming unit for calculating intensity distribution of the reflection light in an emission direction of the measuring light and for forming a tomographic image of the subject of measurement based on the intensity distribution by rendering the reflection light from the subject of measurement, which was obtained by the probe to have interference with the reference light;
    a light path length when exerting interference between the standard light and the reference light is approximately equal to a light path length when exerting interference between the reference light and the reflection light;
    a calculation unit which calculates time change of coherent light data obtained by exerting interference between the standard light and the reference light, wherein coherent light intensity is obtained based on the time change of the coherent light data calculated by the calculation unit;
    a judgment unit for judging a state of the light path for transmitting the reference light based on the coherent light intensity, wherein the judgment unit judges that the state of the light path for transmitting the reference light is not normal when a degree of deterioration of the coherent light intensity with respect to a predetermined reference intensity exceeds a predetermined threshold; and
    a display unit for graph-displaying the time change of the coherent light data calculated by the calculation unit.

11. The optical coherent tomography diagnostic apparatus according to claim 8, further comprising a display unit for graph-displaying degree of attenuation of the intensity of the coherent light data with respect to the amount of deviation from a position at which the light path lengths of the standard light and the reference light are equal.

12. In an optical coherent tomography diagnostic apparatus which splits light outputted from a light source into a measuring light and a reference light, emits the measuring light in a direction of emission to a subject of measurement through a probe inserted into a body cavity, obtains a reflection light from the subject of measurement, and thereafter calculates intensity distribution of the reflection light in the direction of the emission of the measuring light by exerting interference between the reflection light and the reference light and forms a tomographic image of the subject of measurement based on an intensity distribution, the improvement comprising:
    a splitter for further splitting the light outputted from the light source to obtain a standard light;
    a light path connected to the splitter along which is transmitted the standard light and in which a light path length until the standard light exerts interference on the reference light is approximately equal to a light path length until the reference light exerts interference on the reflection light; and
    a calculation unit for calculating time change of coherent light data obtained by rendering the standard light to have interference with the reference light;
    wherein the standard light path does not have a movable portion for varying the light path length.

* * * * *